US012654013B2

(12) United States Patent
Fried et al.

(10) Patent No.: US 12,654,013 B2
(45) Date of Patent: Jun. 16, 2026

(54) MEMORY ENHANCEMENT BY PREFRONTAL DEEP BRAIN STIMULATION SYNCHRONIZED TO MEDIAL TEMPORAL LOBE DURING SLEEP

(71) Applicants: THE REGENTS OF THE UNIVERSITY OF CALIFORNIA, Oakland, CA (US); RAMOT at Tel Aviv University Ltd., Tel Aviv (IL); Itzhak Fried, Los Angeles, CA (US); Yuval Nir, Tel Aviv (IL); Maya Geva-Sagiv, Oakland, CA (US)

(72) Inventors: Itzhak Fried, Los Angeles, CA (US); Yuval Nir, Tel Aviv (IL); Maya Geva-Sagiv, Oakland, CA (US)

(73) Assignees: The Regents of the University of California, Oakland, CA (US); Ramot at Tel Aviv University Ltd., Tel Aviv (IL)

( * ) Notice: Subject to any disclaimer, the term of this patent is extended or adjusted under 35 U.S.C. 154(b) by 159 days.

(21) Appl. No.: 18/563,692

(22) PCT Filed: May 24, 2022

(86) PCT No.: PCT/US2022/030751
§ 371 (c)(1),
(2) Date: Nov. 22, 2023

(87) PCT Pub. No.: WO2022/251234
PCT Pub. Date: Dec. 1, 2022

(65) Prior Publication Data
US 2024/0238594 A1     Jul. 18, 2024

Related U.S. Application Data

(60) Provisional application No. 63/192,419, filed on May 24, 2021.

(51) Int. Cl.
*A61N 1/36*          (2006.01)

(52) U.S. Cl.
CPC ..... *A61N 1/36092* (2013.01); *A61N 1/36064* (2013.01); *A61N 1/36139* (2013.01);
(Continued)

(58) Field of Classification Search
CPC ............ A61N 1/36064; A61N 1/36082; A61N 1/36092; A61N 1/36135; A61N 1/36139;
(Continued)

(56) References Cited

U.S. PATENT DOCUMENTS

| | | | |
|---|---|---|---|
| 6,016,449 A | 1/2000 | Fischell et al. | |
| 2007/0213786 A1 | 9/2007 | Sackellares et al. | |

(Continued)

OTHER PUBLICATIONS

The Regents of the University of California, PCT/US2022/030751, International Search Report and Written Opinion, Aug. 22, 2022, 14 pgs.

(Continued)

*Primary Examiner* — Amanda K Hulbert
(74) *Attorney, Agent, or Firm* — Morgan, Lewis & Bockius LLP

(57) ABSTRACT

A closed-loop neuromodulatory system comprises one or more processors and memory. The system is configured to record signals from a first region of a brain of a human subject during sleep via a first electrode. The system is configured to determine, from the recorded signals, active periods of the first region. The system is configured to stimulate a second region of the brain, different from the first region, during the active periods via a second electrode that is electrically coupled to the first electrode via closed-loop control.

20 Claims, 18 Drawing Sheets

(52) U.S. Cl.
CPC ..... *A61N 1/36157* (2013.01); *A61N 1/36171*
(2013.01); *A61N 1/36175* (2013.01)

(58) Field of Classification Search
CPC ............ A61N 1/36157; A61N 1/36167; A61N
1/36171; A61N 1/36175
See application file for complete search history.

(56) References Cited

U.S. PATENT DOCUMENTS

| | | | |
|---|---|---|---|
| 2017/0014630 A1* | 1/2017 | Fried ................. | A61N 1/36139 |
| 2017/0113046 A1 | 4/2017 | Fried et al. | |
| 2019/0126033 A1* | 5/2019 | Pradeep .............. | A61B 5/4812 |

OTHER PUBLICATIONS

The Regents of the University of California, PCT/US2022/030751, International Preliminary Report on Patentability, Nov. 23, 2023, 9 pgs.

* cited by examiner

FIGURE 3
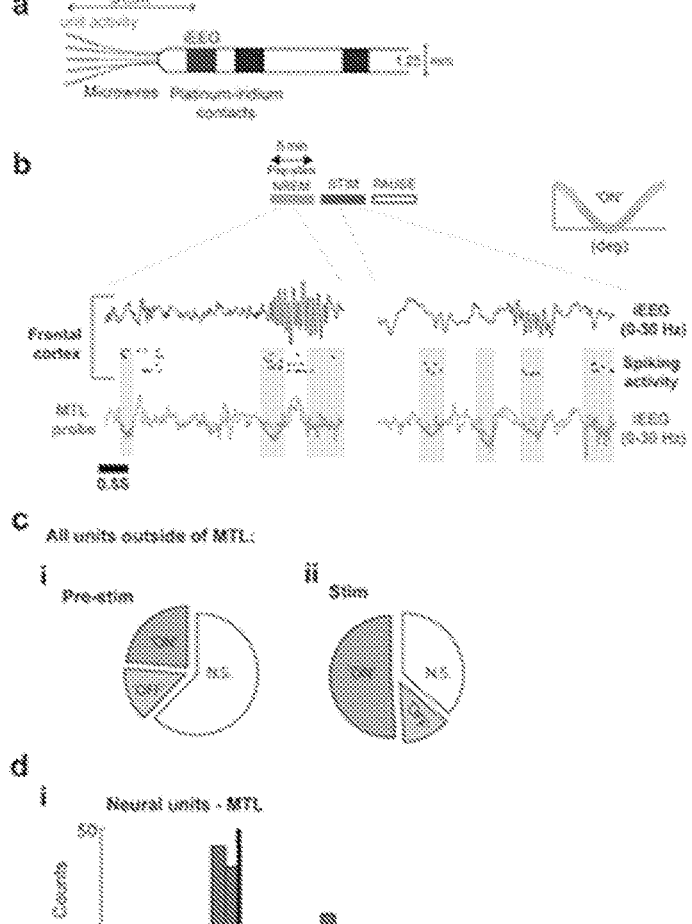
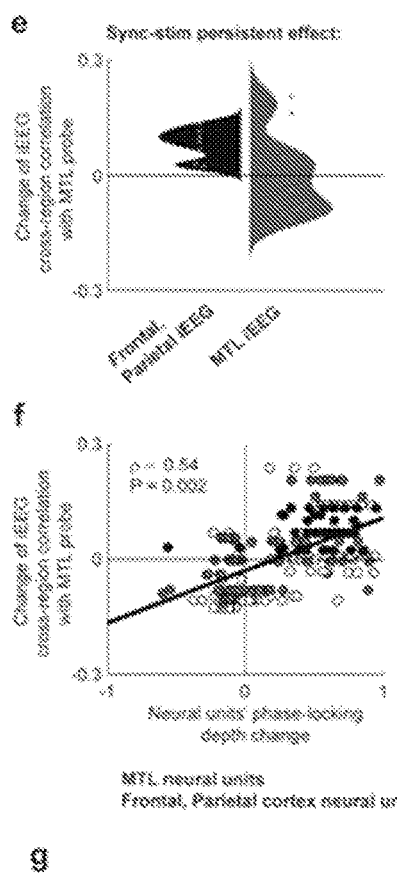
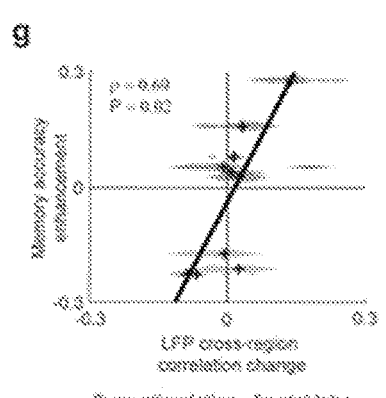

FIGURE 7
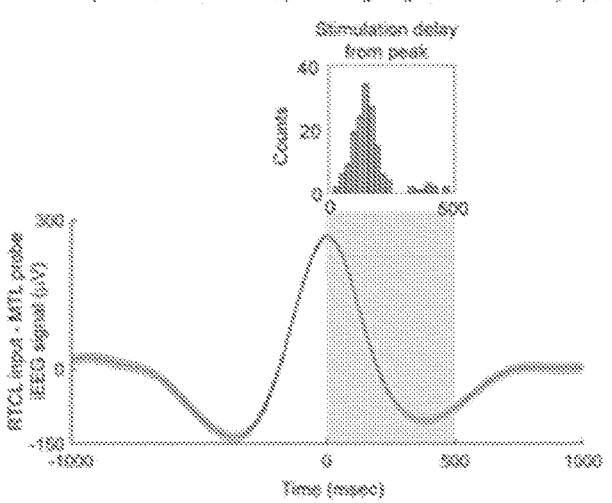 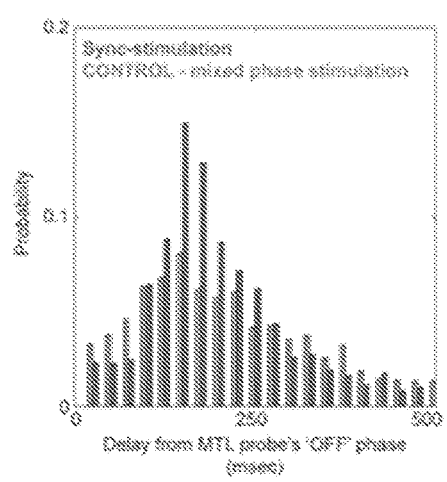
FIGURE 8
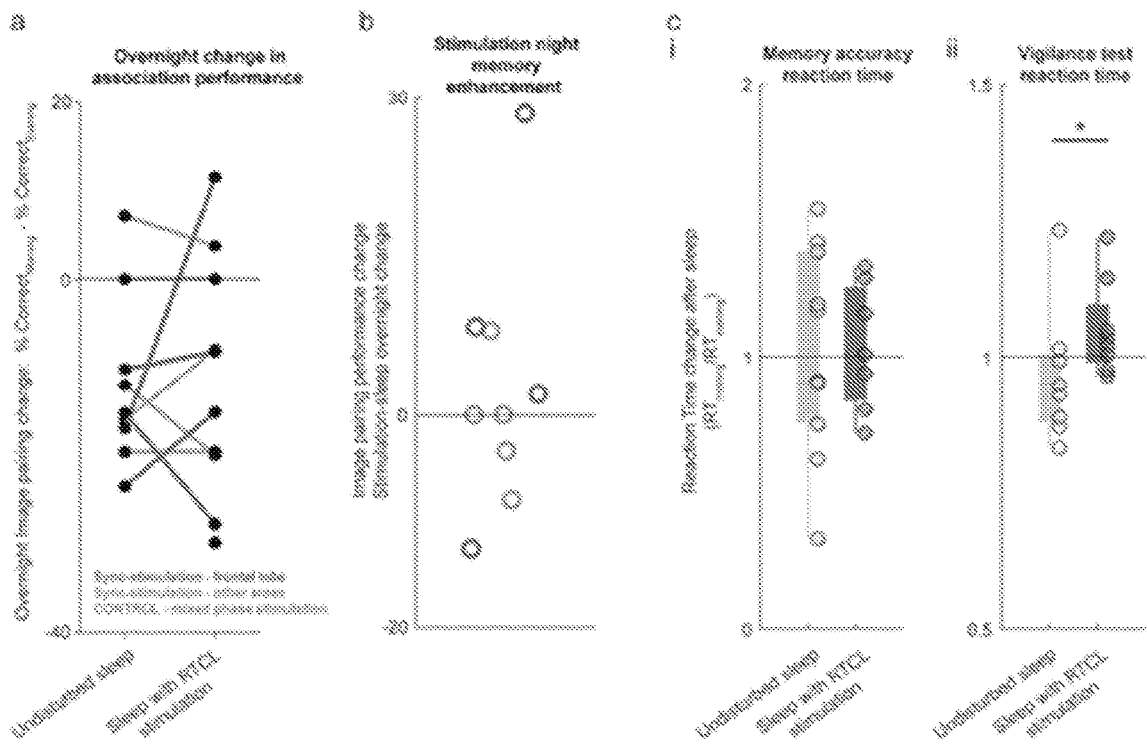

FIGURE 10
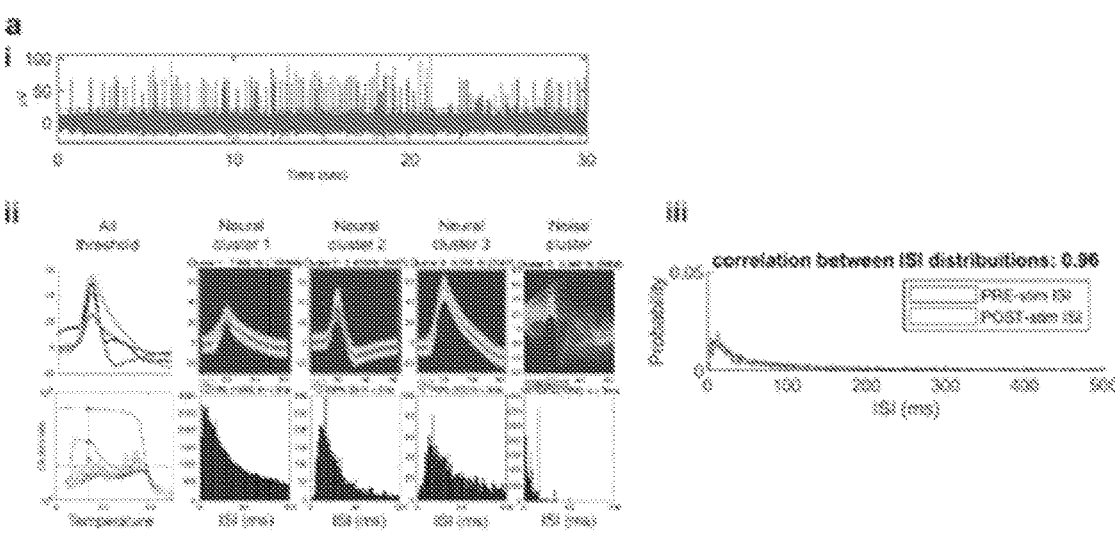
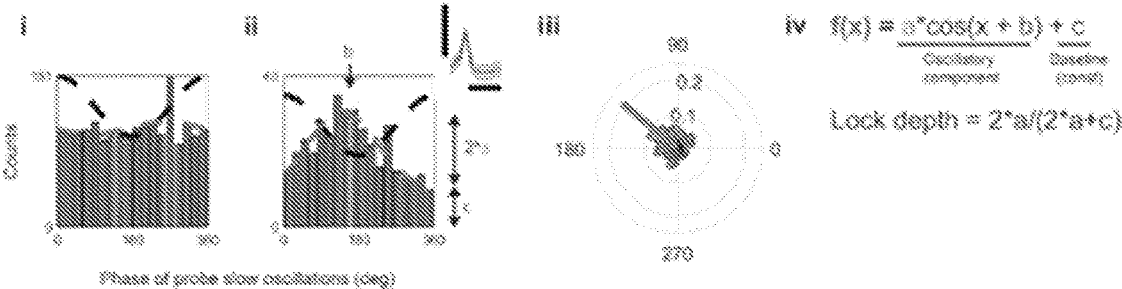
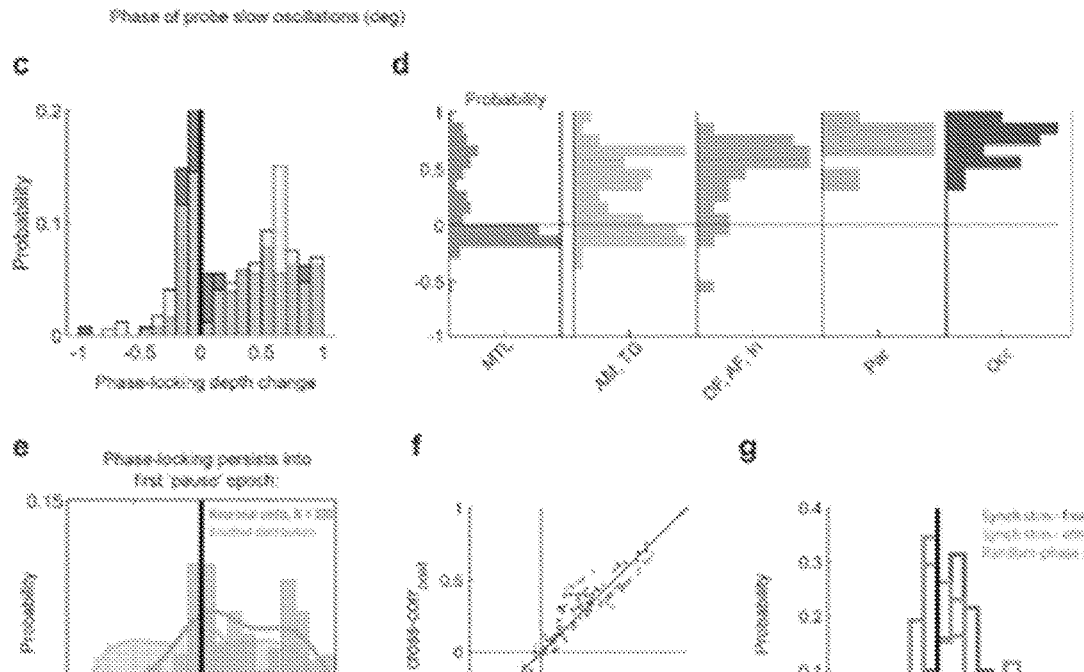

FIGURE 13
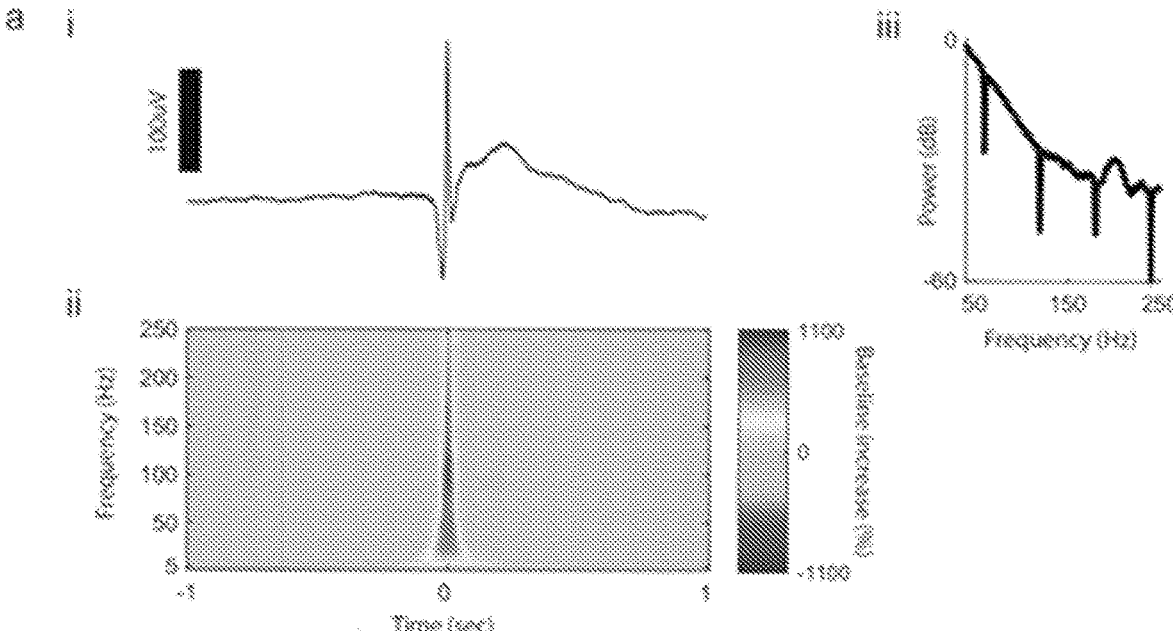
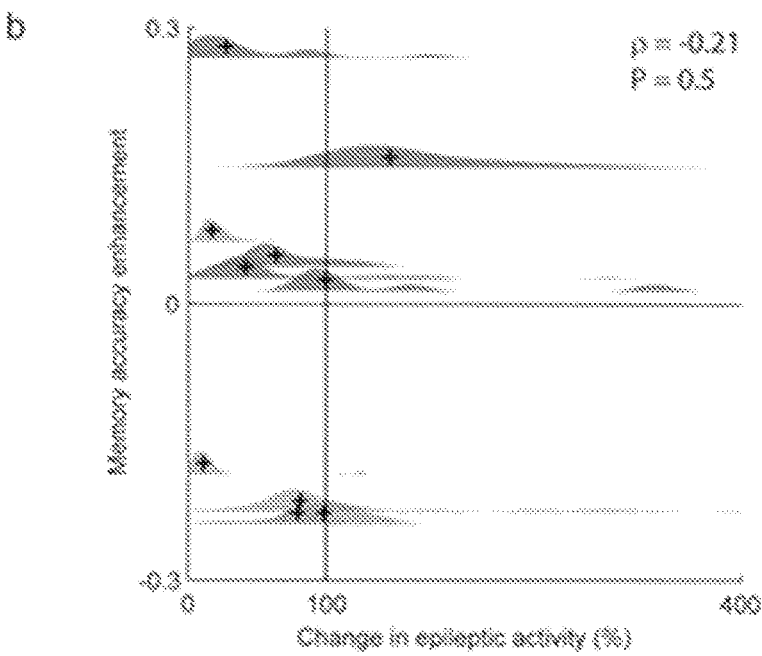

FIGURE 14

| Participant id | Age | Gender | Handedness | Seizure Onset | Resection/Outcome | FDG-PET | MRI |
|---|---|---|---|---|---|---|---|
| 1 | 23 | F | R | Broad right fronto-temporal onset | No surgery | RPHG and R-parietal hypometabolism | Normal |
| 2 | 33 | M | R | R frontal lobe and R SMA(pre) | R frontal resection, seizure free. | Normal | Normal |
| 3 | 33 | F | R | Left mesial areas | RNS in LTL, no improvement | LTL hypometabolism | Normal |
| 4 | 38 | M | L | R medial temporal lobe | R anteromesial temporal lobectomy, significant improvement | R-frontal and R-parietal hypometabolism | structural abnormalities superior parietal and middle frontal lobes |
| 5 | 47 | F | R | LiT gyrus spreading to LaFSG and LIN | RNS in L MTL, seizure free | LTL hypometabolism | LTL structural abnormality |
| 6 | 34 | F | R | Lateral RIO, mesial RPNH | RNS in RIO and RPNH, significant improvement | Basal and Rp periventricular nodule hypometabolism | Bilateral periventricular nodular heterotopia |
| 7 | 36 | M | R | R posterior temporal-anterior occipital region | R temporo-occipital resection, seizure free | Normal | Normal |
| 8 | 34 | F | R | Bilateral temporal | Bilateral longitudinal RNS in hippocampus, significant deterioration | Bilateral MTL hypometabolism | Bilateral hippocampal sclerosis |
| 9 | 29 | F | R | Bilateral mesial R > L, RTL origin in R sided seizures | RNS placed bilaterally in orthogonal fashion, MTL, significant improvement | R-temporal hypometabolism | Normal |
| 10 | 44 | M | R | Broad activity over R frontal and parietal lobes, and RIN, spreads to R temporal gyrus and anterior RIN | RNS spaced widely over insula, significant improvement | R-parieto-occipital cortex hypometabolism | Normal |
| 11 | 35 | M | R | LaFSG and LOBIN | RNS in LaFSG and LOBIN, some improvement | LTL hypometabolism, L-dorsal-striatum mild hypometabolism | Normal |
| 12 | 31 | F | R | L SMA spreads to RIN, bilateral SMA and L anterior frontal | RNS in RIN, and L SMA, some improvement | Normal | Normal |
| 13 | 25 | F | R | R MTL | RNS in R MTL and LFSG, to be determined | LTL hypometabolism | L-hippocampal sclerosis |
| 14 | 32 | M | R | Bilateral MTL | RNS in bilateral MTL, with longitudinal leads in bilateral middle hippocampus, to be determined | LTL subtle hypometabolism | L-hippocampal sclerosis |

| Participant id | session id | start of session time of day | # of stimulation blocks | total session length (min) | stimulation type (b = bipolar, u = unipolar) | stimulation hemisphere* | RTCL input (probe) site** | N iEEG electrodes | intervention type (S = sync-stim, M = mixed phase) |
|---|---|---|---|---|---|---|---|---|---|
| 1 | 1 | 12:15AM | 5 | 86 | b | RH (prefrontal) | mixture of RMH and LMH | 10 | M |
| 2 | 2 | 12:09AM | 7 | 94 | b | LH (prefrontal) | LEC | 10 | S |
| 3 | 3 | 11:30PM | 10 | 96 | b | RH (prefrontal) | R ant-hip | 8 | S |
| 4 | 4 | 2:00AM | 8 | 118 | b | LH (prefrontal) | LPHG | 12 | S |
| 5 | 5 | 12:05AM | 8 | 55 | b | RH (temporal) | RAH | 9 | S |
| 6 | 6 | 2:09AM | 8 | 87 | u | RH (temporal) | RAH | 10 | S |
| 7 | 7 | 11:35PM | 10 | 100 | u | RH (orbital) | RMH | 9 | S |
| 8 | 8 | 10:50PM | 13 | 55 | u | RH (prefrontal) | RMH | 10 | M |
| 9 | 9 | 11:00:00PM | 11 | 90 | u | LH (prefrontal) | LAH | 10 | S |
| 10 | 10 | 12:25AM | 10 | 55 | u | LH (prefrontal) | LMH | 10 | M |
| 11 | 11 | 1:50AM | 6 | 163 | u | LH (prefrontal) | RAH | 12 | M |
| 12 | 12 | 23:30PM | 6 | 45 | u | RH (prefrontal) | RAH | 13 | M |
| 12 | 13 | 2:15AM | 8 | 132 | u | RH (prefrontal) | RAH | 13 | M |
| 13 | 14 | 2:35AM | 6 | 112 | u | RH (prefrontal) | RAH | 10 | S |
| 14 | 15 | 3:45AM | 5 | 59 | u | RH (prefrontal) | RMH | 9 | S |

MEMORY ENHANCEMENT BY PREFRONTAL DEEP BRAIN STIMULATION SYNCHRONIZED TO MEDIAL TEMPORAL LOBE DURING SLEEP

CROSS REFERENCE TO RELATED APPLICATIONS

This Application is a United States National Stage Application filed under 35 U.S.C. § 371 of PCT Patent Application Serial No. PCT/US2022/030751 filed on May 24, 2022, which claims the benefit of and priority to U.S. Provisional Patent Application No. 63/192,419 filed on May 24, 2021, each of which is hereby incorporated by reference in its entirety.

STATEMENT REGARDING FEDERALLY SPONSORED RESEARCH OR DEVELOPMENT

This invention was made with government support under Grant Numbers NS108930 and NS084017, awarded by the National Institutes of Health and Grant Number 1756473, awarded by the National Science Foundation. The government has certain rights in the invention.

TECHNICAL FIELD

The disclosed implementations relate generally to systems and methods for enhancing the human memory, and more specifically, to systems and methods for enhancing the human memory by prefrontal deep brain stimulation synchronized to medial temporal lobe during sleep, and their applications to treatment for Alzheimer's Disease, pathological epileptic activity, and other dementias.

BACKGROUND

Accumulating evidence suggests that sleep is critical for the transformation of initially labile memories into stable representations. Systems-level memory consolidation during sleep is thought to depend on coordinated interplay of neocortical slow waves, thalamo-cortical sleep spindles, and hippocampal ripples, but direct evidence is lacking. A fundamental limitation is the formidable gap between non-invasive cognitive research studying human declarative memory, and mechanistic animal research studying hippocampal activity with single-neuron resolution.

SUMMARY

The present disclosure bridges the gap between non-invasive cognitive research studying human declarative memory and mechanistic animal research studying hippocampal activity with single-neuron resolution, by dynamically manipulating the temporal coordination between sleep activities in the medial-temporal-lobe (MTL) and the neocortex.

Some aspects of the present disclosure describe implementing real-time closed-loop (RTCL) intracranial electrical stimulation in the prefrontal cortex during MTL active periods.

Some aspects of the present disclosure test how this intervention (e.g., RTCL electrical stimulation) affects sleep electrophysiology and overnight consolidation of declarative hippocampal-dependent memory. The experimental results show that synchronizing RTCL stimulation (time-locked to MTL), but not identical stimulation without precise time-locking, result in substantial electrophysiological changes. For example, the synchronized RTCL stimulation enhances neocortical slow waves and sleep spindles, increases locking of brain-wide single neuron activity to MTL slow waves, and improves coupling between MTL-ripples and neocortical oscillations. Furthermore, RTCL stimulation improves memory performance in a manner highly correlated with electrophysiological effects. These results provide the first causal evidence in humans for a role of hippocampo-cortical synchronization during sleep in memory consolidation, indicate that the underlying mechanism involves fine temporal coordination between MTL-ripples and neocortical slow waves and spindles, and suggest potential avenues for treatment of memory disorders during sleep.

The systems, methods, and devices of this disclosure each have several innovative aspects, no single one of which is solely responsible for the desirable attributes disclosed herein.

In accordance with some embodiments of the present disclosure, a method comprises recording signals from a first region of a brain of a human subject during sleep via a first electrode. The method includes determining, from the recorded signals, active periods of the first region. The method includes stimulating a second region of the brain during the active periods via a second electrode that is electrically coupled to the first electrode via closed-loop control.

In accordance with some embodiments of the present disclosure, a closed-loop neuromodulatory system includes one or more processors and memory. The memory stores instructions for execution by the one or more processors. The stored instructions include instructions for: recording signals from a first region of a brain of a human subject during sleep via a first electrode: determining, from the recorded signals, active periods of the first region: and stimulating a second region of the brain, different from the first region, during the active periods via a second electrode that is electrically coupled to the first electrode via closed-loop control.

In accordance with some embodiments of the present disclosure, a system comprises a first implanted electrode and a second implanted electrode electrically coupled to the first implanted electrode via closed-loop control. The system includes one or more processors and memory. The memory storing instructions that, when executed by the one or more processors, cause the processors to: record signals using the first implanted electrode: determine one or more active periods based on the recorded signals: and apply, in real-time, electric pulses that are synchronous with the one or more active periods using the second implanted electrode In accordance with some embodiments, a non-transitory computer-readable storage medium stores one or more programs configured for execution by a computer system having one or more processors and memory. The one or more programs include instructions for performing any of the methods described herein.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

FIG. 1a illustrates experimental design timeline (individual subject statistics are reported in FIGS. 15 and 16). Each subject participated in two overnight sessions (order counterbalanced) with one undisturbed sleep session and another session with real-time closed-loop (RTCL) neocortical stimulation synchronized to medial temporal lobe (MTL) slow wave up-states. Memory was assessed immediately following evening learning and in the morning following night sleep.

FIG. 1b (top) illustrates representative timeline of intervention night along with time-frequency representation (e.g., spectrogram) of iEEG. The warm color (e.g., red, see color-bar on right) mark increased power in specific time-frequency windows (frequency shown on left side of y-axis). Superimposed white lines on top part of panel mark the detection of NREM sleep-state. Note that non-rapid eye movement (NREM) stages N2 and N3 (horizontal white bars) are associated with increased power in spindle (9-16 Hz) and slow-wave (<4 Hz) frequency ranges (black rectangles). Middle: RTCL intervention lasts 45-90 min and consists of alternating 5-min stimulation ('stim') and pause intervals, preceded ('pre-stim') and followed ('post-stim') by intervals used in some subsequent analyses (see Methods). FIG. 1b (bottom) is a schematic illustration of RTCL approach where MTL slow wave up-states (troughs in MTL iEEG, blue: co-occurring with neuronal activity, black) are used to trigger stimulation pulses in neocortex (red).

FIG. 1c illustrates RTCL stimulation verification. FIG. 1c(i) are Coronal MR images denoting MTL synchronization-probe location (blue) and prefrontal DBS site location (red) in participant #3. FIG. 1c(ii) illustrates single-trial MTL probe iEEG signals (voltage-colormap on right): increased voltage in the probe triggers stimulation in a neocortical site. FIG. 1c(iii) illustrates at t=0) sec (patient 4, n 244 stimulations), targeted to the MTL iEEG trough (active state) following the prominent MTL iEEG peak (inactive state). Average and standard error of the mean (SEM) of the MTL probe signal are superimposed on top (black, scale bar denotes 100 μV). FIG. 1c(iii) illustrates average iEEG signal adjacent to the neocortical stimulation site around stimulation pulses (t=0 s).

FIG. 1d illustrates all pairs of MTL probe (blue) and stimulation site electrodes (black), overlaid on a MNI brain (n=14 participants). Line color depicts stimulation type: red, synchronizing stimulation (sync-stimulation) in prefrontal cortex targeted to MTL slow wave up-phase: Orange, sync-stimulation in other (temporal) neocortical regions: Gray, mixed-phase stimulation in prefrontal neocortex.

FIG. 1e illustrates cognitive learning and memory paradigm (see Methods section) included presentation of image pairs of celebrities and animals, followed by assessment of recognition memory (distinguishing celebrities that appeared in learning sessions from celebrity lures) and paired associations (the animal associated with them).

FIG. 1f illustrates overnight change in recognition memory accuracy (Δd') for nine patients tested following two nights: undisturbed sleep (left) vs. following sleep with RTCL stimulation (right). Line colors depict stimulation type, as in D.

FIG. 1g illustrates within-subject difference in recognition memory accuracy (difference in Δd') between overnight changes in intervention night and undisturbed sleep (the difference between black circles in FIG. 1f): 6 out of 7 patients with sync-stimulation (red, orange) showed superior performance in stimulation nights (Stimulation–Sleep>0), while no subject with mixed-phase stimulation (gray) shows this effect

FIG. 2a(i) shows representative average time-frequency response (TFR, or spectrogram) in an orbitofrontal cortex iEEG electrode across all sync-stimulation trials demonstrates a prominent increase in spindle power (9-16 Hz, white rectangle: See Methods section) relative to 1-sec epochs before stimulation (t=0) sec). Colors depict % increase (colorbar on right). FIG. 2a(ii) illustrates spindle power enhancement across the entire dataset (n=335/215 iEEG channels from subjects undergoing sync-stimulation (red)/mixed-phase stimulation (gray), respectively). Enhancement index=mean of [stimulationTFR$_{ROI}$–baselineTFR$_{ROI}$], where baselineTFR represents % change for sham-stimulation-moments (See Methods section). The sync-stimulation group (red) exhibited elevated spindle power compared to sham-moments (P<10$^{-16}$) not observed in the mixed-phase group (gray, n.s.); the difference between groups was highly significant (Wilcoxon rank sum test, red versus gray: ***P<10$^{-17}$). Distributions are smoothed using ksdensity (Matlab, Mathworks) with a Normal kernel. Black '+' denotes the median of each distribution.

FIG. 2b illustrates examples of spindles in two participants: representative activities in simultaneously recorded iEEG electrodes across different brain regions demonstrating spindles (cyan stars) occurring shortly after stimulation (t=0) sec). Blue trace at bottom ('MTL probe')—filtered [0.5-2] Hz MTL iEEG channel used as probe to determine stimulation timing, superimposed with active-phase depiction (90-270°, pink) versus inactive phases (brown): Black traces—filtered [0-30] Hz iEEG in other brain regions (R—right, L—left, OF—orbitofrontal cortex, EC—entorhinal cortex, AH—anterior hippocampus, A—Amygdala, PHG—parahippocampal gyrus).

FIG. 2c illustrates distributions of differences in spindle detection probability during 3-sec following stimulations relative to sham-stimulation control points (plotted as in FIG. 2a(ii), see Methods Section): These distributions reveal increased probability in subjects undergoing sync-stimulation in OF (red) and decreased probability for mixed-phased stimulation (gray). Wilcoxon sign rank test for red distribution: P<10$^{-14}$: for gray distribution: P<10$^{-10}$. Wilcoxon rank sum comparing both distributions: ***P<10$^{-25}$.

FIG. 2d illustrates the increase in spindle detection probability is widespread across cortical territories in both hemispheres regardless of stimulation location. Each circle marks one iEEG electrode, whose color corresponds to spindle-detection probability increase relative to sham-control points, computed as in FIG. 2c (color-bar on right): contact location overlaid on an MNI brain. Note largest effects in the prefrontal cortex.

FIG. 2e illustrates memory accuracy enhancement per subject (y-axis, stimulation night relative to undisturbed sleep night, values as in FIG. 1g) vs. individual immediate effect of spindle increase (x-axis, quantified as $$\frac{P_{stim} - P_{sham}}{P_{stim} + P_{sham}}$$

in the 3-sec following stimulation) reveals significant correlation (Spearman correlation: ρ=0.83, P=0.002, n=10 subjects). The distribution for each subject across all iEEG contacts is shown: black crosses mark the mean spindle enhancement in each subject. Red, sync-stimulation in prefrontal cortex. Orange, sync-stimulation in other neocortical regions. Gray, mixed-phase stimulation in prefrontal cortex.

Figure 2:
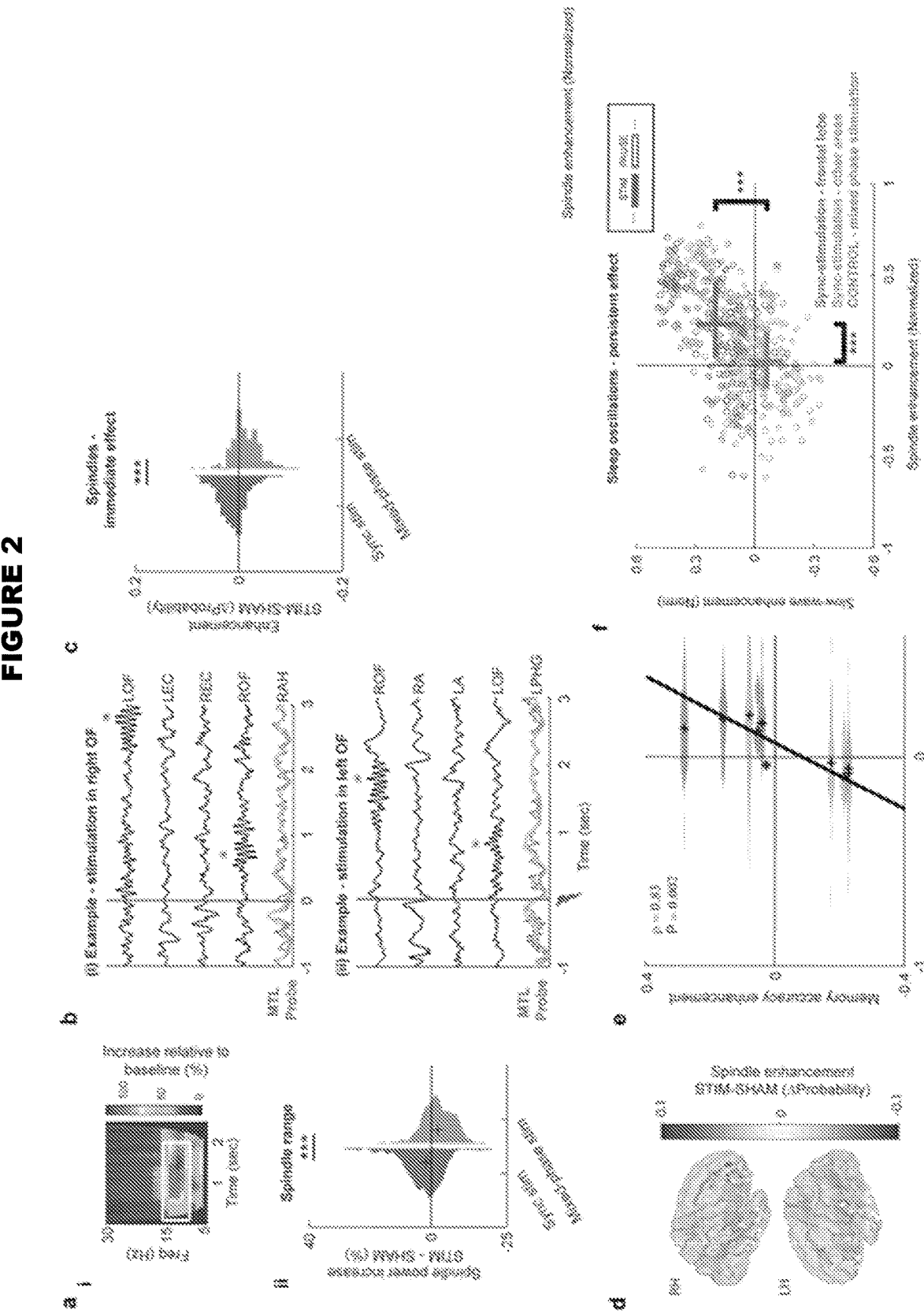
FIGS. 2a-2f illustrate synchronizing stimulation enhancement of slow waves and sleep spindles correlates with memory accuracy improvements.

FIG. 2f illustrates persistent effect: Correlated iEEG slow-wave rate enhancement (y-axis) and spindle rate enhancement (x-axis) occurs in sync-stimulation subjects (red, orange) but not in mixed-phase subjects (gray). Each circle marks one iEEG contact (N=240/78/207 iEEG contacts for red/orange/gray groups, respectively). Shown is the contrast index for slow-wave or spindle rate during 1min following stimulation blocks (post-stim) relative to the remaining 'pause' blocks:

$$\frac{\text{Event rate}_{post-stim} - \text{Event rate}_{pause}}{\text{Event rate}_{post-stim} + \text{Event rate}_{pause}}.$$

Statistical comparison between contrast indices of sync-stimulation (all locations) and mixed-phase groups—Wilcoxon rank-sum test: ***P<$10^{-16}$, P<$10^{-65}$ for spindles and slow waves, respectively. Red/gray whiskers depict 25-75$^{th}$ percentile for both groups.

FIGS. 3a-3g illustrate neuronal spiking across the brain phase-locks to MTL slow wave activity following synchronizing stimulation.

FIG. 3a is an illustration of flexible depth electrodes used for simultaneous recording of iEEG (platinum contacts, blue and black) and unit spiking activity (recorded on microwires, green).

FIG. 3b illustrates two representative examples showing 4-sec of spiking activities in prefrontal cortex during sleep. Rows (top to bottom) show orbitofrontal cortex iEEG (black trace), spiking in four neuronal unit clusters (black ticks), and MTL probe iEEG (blue trace) superimposed with slow-wave active-phase (90-270°, 'ON', pink) versus inactive phases ('OFF', brown). iEEG traces are filtered between [0-30] Hz. Left: activity before stimulation is scattered relative to MTL ON/OFF phases. Right: activity becomes phase-locked to MTL active phase (pink) during stimulation block.

FIG. 3c illustrates percentage of neural clusters recorded outside of MTL (n=201) with significant phase-locking to MTL-probe slow-wave 'ON' phase (Methods). Pink/brown colors as in FIG. 3b. White, non-significant phase-locking. Percentage of clusters locked to 'ON' increased from (i) 23.6% during pre-stimulation baseline ('pre-stim', left pie chart) to (ii) 51.1% during stimulation block ('stim', right pie chart).

FIG. 3d shows distributions of the increase in phase-locking of neural units to the MTL-probe slow-wave oscillation, quantified for each unit as the change in locking-depth (LD):

$$\frac{LD_{stim} - LD_{pre\,stim}}{LD_{stim} + LD_{pre\,stim}}$$

(Methods, FIG. 10b). These distributions are shown separately for: (i) MTL and temporal-gyrus clusters (top, blue, n=183, P=0.3): (ii) Neocortical (orbitofrontal/anterior pre-frontal/parietal/occipital) clusters (black, n=64, P<$10^{-13}$): P values via signtest. Direct comparison of distributions Wilcoxon ranksum test: P<$10^{-12}$.

FIG. 3e illustrates iEEG cross-regional correlation increase persists during 'pause' block: shown is the change in correlation between medial iEEG contact (blue contact in FIG. 3a, closest to neural units recording site) and MTL probe iEEG, revealing an increase following first NREM sync-stimulation block for prefrontal and parietal iEEG electrodes (black distribution, Wilcoxon sign rank test: P=0.01, n=7 iEEG electrodes) but not for MTL iEEG contacts (blue distribution, Wilcoxon sign rank test: P=0.7, n=13 iEEG electrodes).

FIG. 3f illustrates enhanced phase-locking of neural units to MTL slow oscillations is correlated with increased cross-regional correlations between iEEG signals: Scatter plot of increase in MTL-neocortical iEEG correlation (y-axis) versus change in locking-depth of spiking activity to MTL iEEG slow oscillations (x-axis). Each circle denotes an iEEG electrode (blue-filled circles, MTL: gray circles, OF/Par: white circles, other). Scatterplot reveals a significant correlation (Spearman correlation: ρ=0.55, P=0.002, iEEG correlation was calculated for the medial contact of each electrode and the MTL probe, vs median depth-locking change for neural units recorded on the vicinity of iEEG contact, n=29 iEEG electrodes).

FIG. 3g illustrates memory enhancement per subject (y-axis, difference between sleep with RTCL stimulation versus undisturbed sleep) significantly correlates with enhancement in MTL-neocortical cross-regional iEEG correlation following the first stimulation blocks (x-axis, Methods, n=10 patients, Spearman correlation ρ=0.69, P=0.02). Black crosses mark the mean of each patient's correlation change values across all iEEG contacts (Methods, shown as distribution). Sync-stimulation—red in prefrontal cortex and orange in other neocortical regions. Gray, mixed-phase stimulation in prefrontal cortex.

FIGS. 4a-4e illustrate synchronizing stimulation increases triple co-occurrence of MTL ripples, neocortical slow-waves and spindles.

Figure 4:
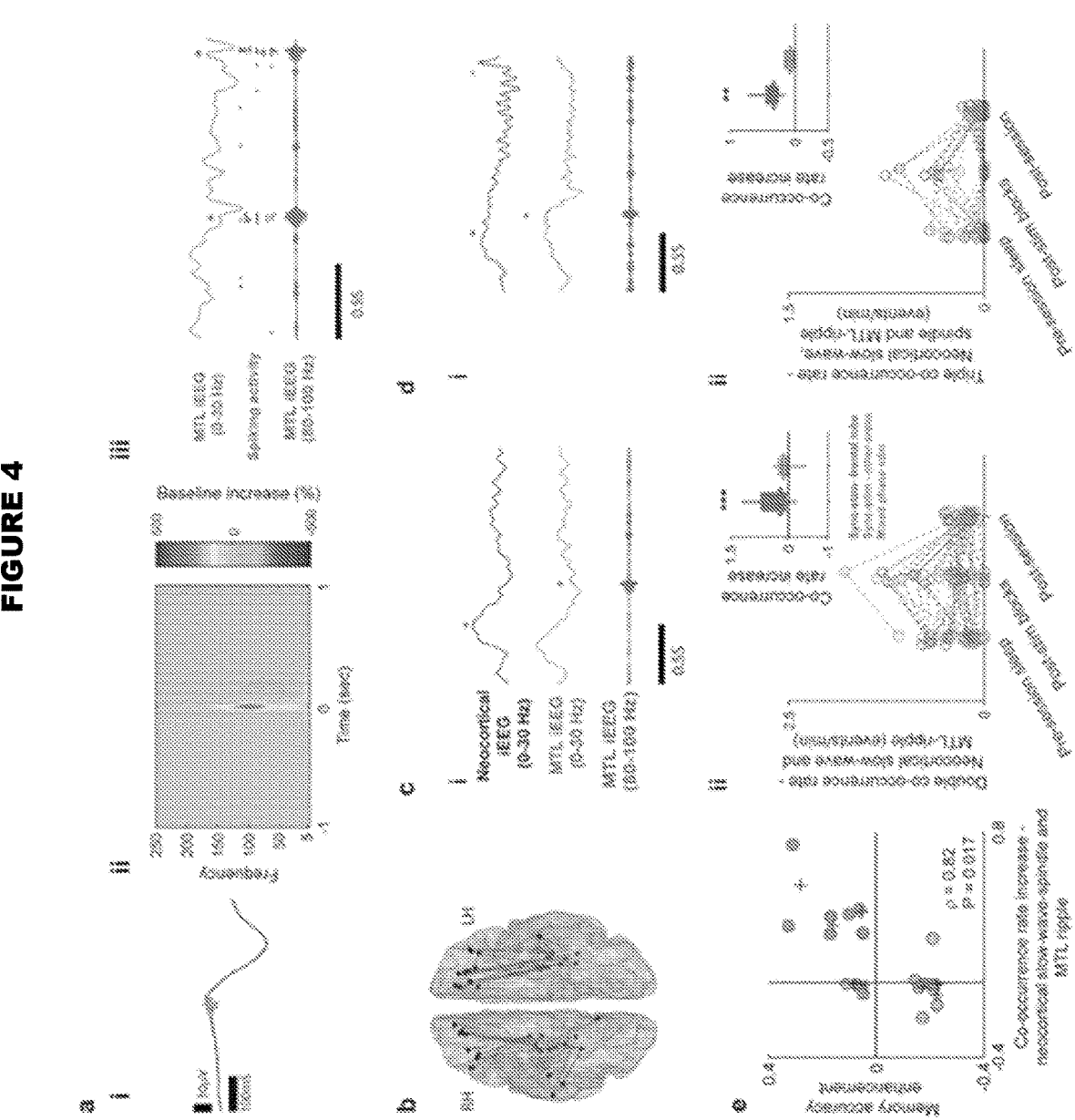

FIG. 4a(i) illustrates a grand average of unfiltered iEEG traces (mean±SEM, n=7308 ripple detections in 31/13 iEEG channels/subjects), aligned to the maximum ripple peak. Scale bars denote 100 ms (x-axis) and 30 μV (y-axis). FIG. 4a(ii) illustrates average ripple-peak-locked TFR spectrogram (% change from pre-event baseline, colorbar on right) highlights the band-limited frequency profile of detected ripples. FIG. 4a(iii) illustrates an example of ripple detections in MTL iEEG (parahippocampal gyrus): top iEEG signal is filtered between [0-30] Hz and bottom trace between [80-100] Hz. Middle row, corresponding spiking activities on adjacent micro-electrodes (green microwire electrodes in FIG. 3a). Brown asterisks denote detected iEEG ripples (blue electrode contact in FIG. 3a).

FIG. 4b illustrates all pairs of neocortical (black) and MTL (blue) iEEG electrodes included in MTL-neocortical co-occurrence analysis (c-d), overlaid on an MNI brain (see Methods Section: n=37 iEEG electrode pairs, 11 subjects). Line colors depict stimulation type: red: sync-stimulation in orbitofrontal cortex: orange: sync-stimulation in other neocortical regions: gray: mixed-phase stimulation in orbitofrontal cortex.

FIG. 4c illustrates MTL-ripples co-occurring with neocortical slow waves (see Methods Section): FIG. 4c(i) is an example showing representative simultaneous recording of neocortical slow wave (top, black trace: purple asterisk shows positive iEEG peak/inactive phase of slow wave) and MTL ripple (middle and bottom, blue traces: brown asterisk shows detected ripple). Top two iEEG signals are filtered between [0-30] Hz and bottom trace between [80-100] Hz. FIG. 4c(ii) illustrates MTL ripple-neocortical slow wave co-occurrence incidence across entire dataset: co-occurrence increase in the 1-min interval post-stimulation blocks (middle) relative to pre-sleep (left) and post-sleep (right) blocks. Inset, increase relative to average of pre- and post-sleep values (red, n=22 electrode pairs, ***P<10^{-3} in sync-stimulation group: gray, n=11, P=0.12 in mixed-phase group: Wilcoxon signed-rank tests).

FIG. 4d illustrates triple co-occurrence of MTL-ripples with neocortical slow waves and spindles (Methods Section). FIG. 4d(i) illustrates representative simultaneous recording of neocortical slow wave (top, black trace: purple asterisk shows positive iEEG peak/inactive phase of slow wave and pink asterisk shows detected spindle) and MTL ripple (middle and bottom, blue traces: brown asterisk shows detected ripple). Signals are filtered as in FIG. 4c. FIG. 4d(ii) illustrates incidence of triple co-occurrence of MTL ripples-neocortical slow waves-spindles across entire dataset: incidence increases 1-min post stimulation-blocks (middle) relative to pre-session sleep (left) and post-session sleep blocks (right: see block structure in FIG. 1b). Inset, increase relative to average of pre- and post-sleep values (red, n=7 electrode pairs, **P<10^{-2} in sync-stimulation group: gray, n=2, P=0.5 in mixed-phase group: Wilcoxon signed-rank tests).

FIG. 4e illustrates a scatter plot of change in memory accuracy following the intervention-night as compared to undisturbed sleep (y-axis) versus the increase of triple co-occurrence between MTL ripples-neocortical slow waves-spindles (x-axis) reveals significant correlation (n=19 MTL-neocortical electrode pairs in 8 patients, Spearman correlation over the median values for each patient [marked by black cross], $\rho$=0.82, *P=0.017). Marker outer color: brown, electrode pair located in stimulated hemisphere: teal, electrode pair located in the contralateral hemisphere.

FIGS. 5a-5d illustrate automated scoring of NREM sleep intervals based on iEEG.

FIG. 5a illustrates a representative time-frequency decomposition (spectrogram) of overnight orbitofrontal cortex iEEG activity, used for sleep scoring in participant #3. The spectrogram was computed with short-time Fourier transform (30 sec window; no overlap, 0-40 Hz range), and additional normalization by a 2D Gaussian filter ($\sigma$=3) was used for visualization purposes (but not for NREM scoring). Black rectangles mark the frequency bands used for NREM detection: slow wave band (0.5-4 Hz), and sigma band (9-16 Hz) for sleep spindles. White dots mark time-points scored as NREM sleep.

FIG. 5b illustrates a scatter plot of sigma power (y-axis) versus slow-wave power (x-axis) for participant #3. Each dot marks a 30 sec epoch, and its color denotes either NREM or desynchronized (REM sleep/wakefulness) labels, according to the maximum posterior probability of a 2-component Gaussian mixture fit to the entire dataset. Red, NREM sleep: Green, desynchronized states (wakefulness/REM sleep).

FIG. 5c illustrates an iEEG power spectrum for each vigilance state for participant #3. Red, NREM sleep. Green, overnight desynchronized states (REM sleep or sporadic wake intervals). Gray, unequivocal wakefulness periods occurring before or after the overnight sleep session. Note that iEEG power spectrum during overnight desynchronized states (green) resembles that found for unequivocal wakefulness (gray).

FIG. 5d(i) illustrates a grand mean iEEG power spectrum over all participants for all sleep/wake stages superimposed (n=15 overnight sessions). Colors as in FIG. 5c. FIG. 5d(ii) shows a power spectrum separately for NREM sleep. FIG. 5d(iii) shows a power spectrum separately for overnight desynchronized states (REM sleep or sporadic wake intervals). FIG. 5d(iv) shows a power spectrum separately for unequivocal wakefulness periods occurring before or after the overnight sleep session.

Figure 6:
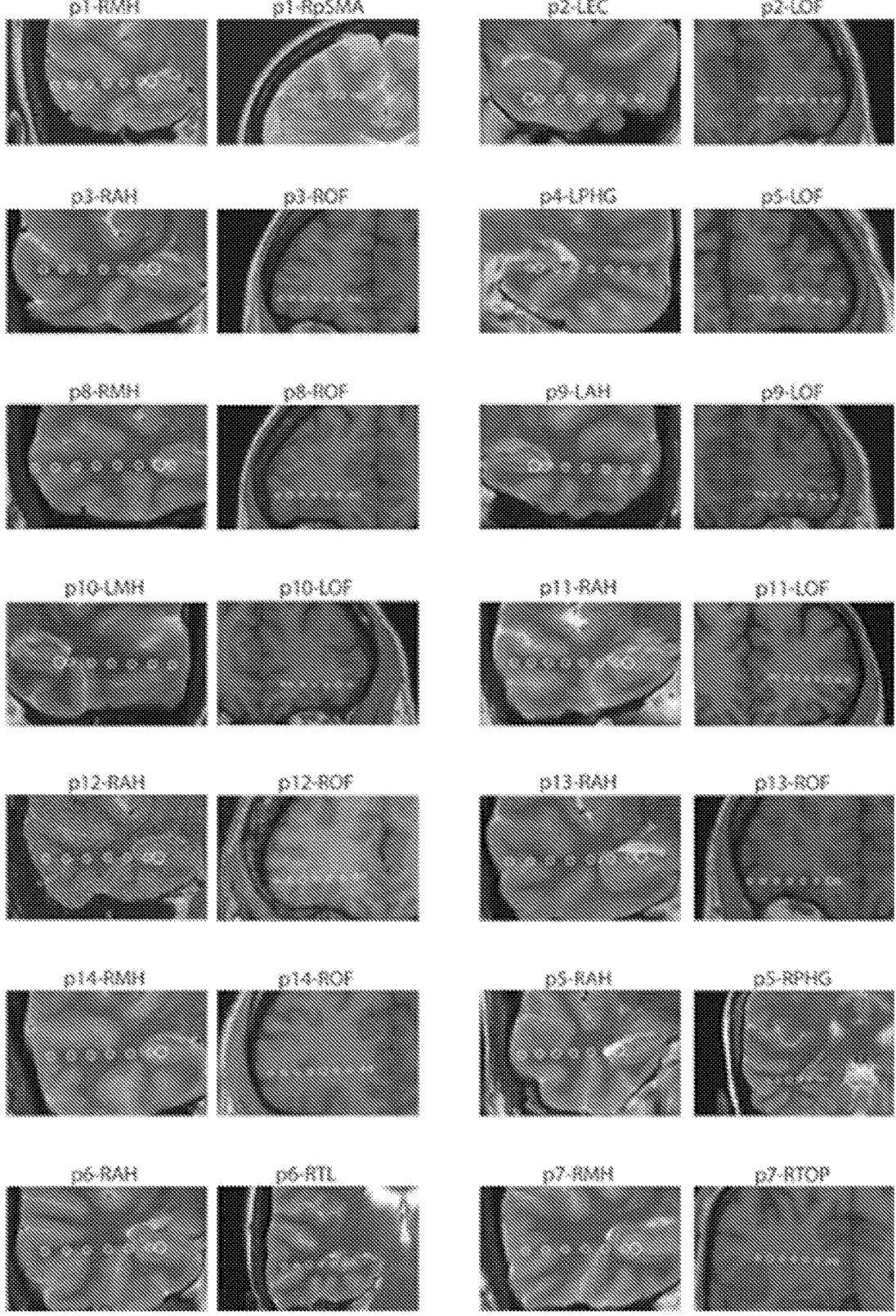

FIG. 6 illustrates location of MTL synchronization-probe and neocortical stimulation iEEG electrodes. For each participant (p 1-14) two coronal MR images denote MTL synchronization-probe for closed-loop control (left image, blue circles) and neocortical stimulation site (right image, red circles), yellow circles depict other iEEG contacts on the depth electrode. Title for each MR image: p=participant, number corresponds to participant-id in FIGS. 15 and 16: letters correspond to clinical iEEG label of electrode location. Note that in participants 5-7 the stimulation site was outside the prefrontal lobe. Abbreviations: R=right, L=Left: AH=Anterior Hippocampus (hip), MH=Medial hipocampus, EC=Entorhinal cortex, PHG=Parahippocampal gyrus, TL—temporal lobe, OF—orbitofrontal cortex, TOP—temporal-occipital, pSMA—pre-supplementary motor area.

FIGS. 7a and 7b illustrate a closed loop system.

FIG. 7a illustrates an example from participant #7 showing the average and SEM of MTL probe's iEEG signal (blue trace, filtered between [0.5-4] Hz to highlight slow-wave activity), time-locked to the positive iEEG peak immediately preceding stimulation time (t=0). Note that iEEG peak corresponds to the neuronal inactive slow-wave phase. Top inset: distribution of stimulation delays (n=423 stimulation events) from iEEG slow-wave positive peak for this participant (t=0).

FIG. 7b illustrates an analysis across the entire dataset (n=15 overnight sessions) showing distribution of stimulation delays with respect to immediately preceding MTL iEEG peak (slow-wave inactive phase): red, sync-stimulation: gray, mixed-phase stimulations, Wilcoxson ranksum test between both distributions—P<10^{-30}, Two sample Kolmogorov-Smirnov test—P<10^{-50}).

FIGS. 8a-8c illustrate memory and behavioral measures.

FIG. 8a illustrates participants were asked to recall the animal associated with every person they recognized from the learning session. Pairing index (PI) is quantified as PI=100*correct pairing/all pairing attempts (correct+incorrect). Overnight change $PI_{Morning}$–$PI_{Evening}$ is plotted for patients who were tested following undisturbed sleep (left) and following a sleep with RTCL stimulation (right). Line color depicts stimulation type: red, synchronizing stimulation (targeted to MTL 'on' phase, delivered in prefrontal neocortex (n=5, note that one participant chose not to complete the association test on undisturbed sleep night): orange, synchronizing stimulation (targeted to MTL 'on' phase), delivered in other regions (n=2): gray, mixed-phase stimulation in prefrontal neocortex (n=3). Recall of paired associates did not show significant effects following RTCL stimulation.

FIG. 8b illustrates within-subject difference of overnight change in memory pairing success between intervention night (sleep with RTCL stimulation) and undisturbed sleep (difference between the dots in panel a): 5/6 patients with sync-stimulation (red, orange) showed no change/superior performance in stimulation nights (Stimulation–Sleep>=0), while 1/3 subjects with mixed-phase stimulation (gray) showed this effect.

FIG. 8c(i) illustrates median change in reaction time (RT) for recognized images was not significantly different between intervention nights (red) and undisturbed nights (green) (n=10, P=0.62 via Wilcoxon rank-sum test). No significant correlation was observed between RT change and Δd' (change in recognition accuracy). FIG. 8c(ii) illustrates RT change on a separate psychomotor vigilance task (PVT, Methods), measured as median($RT_{morning}$) divided by median($RT_{evening}$), shows significantly faster performance following undisturbed sleep than after sleep with RTCL stimulation (P<0.05 via Wilcoxon rank-sum test comparing reaction time changes between 8 nights of undisturbed sleep or RTCL sync-stim intervention). The paradigm was similar to that used in Nir et al., "Selective neuronal lapses precede human cognitive lapses upon sleep deprivation," *Nat. Med.* (2017) doi:10.1038/nm.4433, where participants were instructed to respond as quickly as possible to images presented with variable long delays (Methods).

Figure 9:
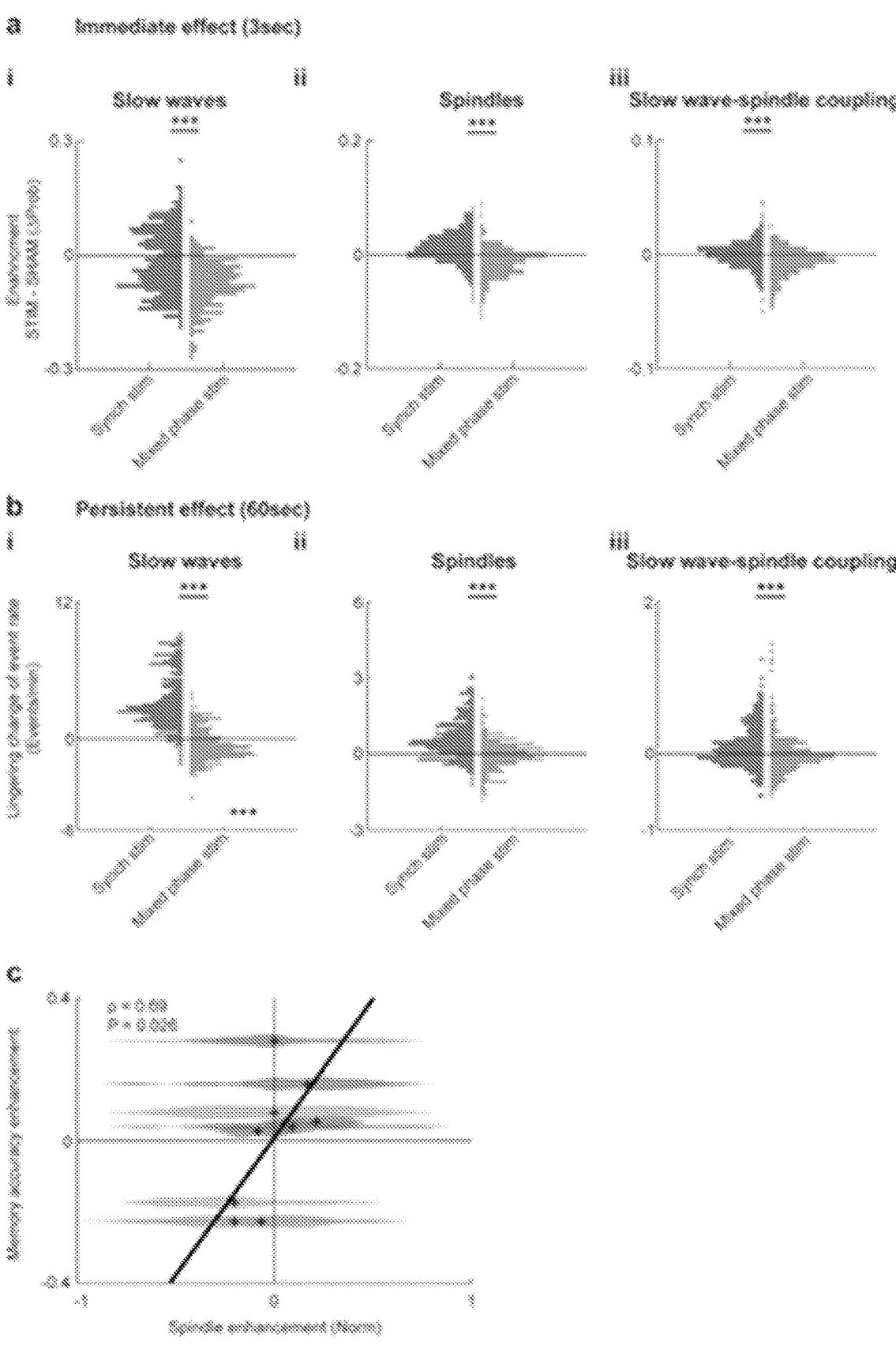

FIGS. 9a-9c illustrate brain-wide change in sleep oscillation rates following sync-stimulation.

FIG. 9a illustrates distributions of immediate change of detection-probabilities for (i) slow-waves (ii) spindles and (iii) slow wave-spindle couples. Probability was calculated in 3-sec intervals immediately following stimulations, relative to SHAM-stimulation control points (as in FIG. 2c, see Method section). These distributions reveal decreased probability in subjects undergoing mixed-phase stimulation in orbitofrontal cortex (gray) vs sync-stimulation patients (red). Wilcoxon rank-sum comparison of both distributions: slow-waves: *P<$10^{-15}$ (n=335/215 iEEG contacts for red/gray groups), spindles: *P<$10^{-23}$ (n=325/211 iEEG contacts for red/gray groups), slow-wave—spindle couples ***P<$10^{-7}$ (n=266/164 iEEG contacts for red/gray groups). N-values differ between panels i-iii because channels with zero detections in one of the conditions were excluded.

FIG. 9b illustrates distributions of persistent changes of detection-rate for (i) slow-waves, (ii) spindles, and (iii) slow wave-spindle couples. Event rates were calculated over 1-min following stimulations-blocks, relative to remaining 'pause' blocks (as in FIG. 2f). These distributions reveal decreased probability in subjects undergoing mixed-phase stimulation in orbitofrontal cortex (gray) vs sync-stimulation patients (red). Wilcoxon rank-sum comparison of both distributions: slow-waves: *P<$10^{-15}$ (n=335/215 iEEG contacts for red/gray groups), spindles: *P<$10^{-23}$ (n=325/211 iEEG contacts for red/gray groups), slow-wave—spindle couples ***P<$10^{-9}$ (n=266/164 iEEG contacts for red/gray groups). N-values differ between panels i-iii because channels with zero detection in one of the conditions were excluded.

FIG. 9c illustrates memory accuracy enhancement (y-axis, stimulation night relative to undisturbed sleep night) versus individual spindle detection increase in the persistent condition (described in (b)), calculated as event rate during 1-min following stimulation blocks (post-stim) relative to the remaining 'pause' blocks:

$$\frac{\text{Event rate}_{post-stim} - \text{Event rate}_{pause}}{\text{Event rate}_{post-stim} + \text{Event rate}_{pause}},$$

reveals significant correlation (Spearman correlation: p=0.69, *P=0.026, n=10 subjects). Shown is the distribution for each subject across all iEEG contacts outside MTL: black crosses mark the mean of each subject. Red, sync-stimulation in prefrontal neocortex. Orange, sync-stimulation in other neocortical regions. Gray, mixed-phase stimulation in prefrontal neocortex.

FIGS. 10a-10g illustrate phase-locking change following stimulation.

FIG. 10a illustrates a spike sorting procedure. FIG. 10a(i) is a representative 30 sec example of high-pass filtered (>300 Hz) microwire LFP signal recorded in prefrontal cortex along with threshold for spike detection (red horizontal line). FIG. 10a(ii) is a screenshot from 'wave-clus' spike-sorting toolbox demonstrating automatic superparamagnetic clustering of wavelet coefficients for 3 clusters as well as other detected events aggregated in the 'noise' cluster (right most side). Top panels: Left—average waveform for each cluster, right—each cluster's waveform (mean and standard deviation) displayed as a heat map: Bottom panels are the 'temperature' index that controls the number of clusters[56], and inter-spike-interval (ISI) distribution for each cluster. FIG. 10a(iii) is an ISI distribution for cluster #1 during pre-stim sleep and post-stim sleep (correlation between distributions is 0.96).

FIG. 10b illustrates a temporal-fit method for spike phase distribution: distribution of spikes from a neural unit recorded in orbitofrontal cortex, across MTL iEEG slow wave phases (i) before any stimulation block ('PRE'), (ii) during the first 'pause' block, demonstrating a persistent effect of the stimulation block. Inset shows average and SEM of action potential waveform during the entire recording session. Calibration bars mark 1 msec and 50 μV. (ii) Same distributions as (i) in blue, and (ii) in red, overlaid on a polar plot, with mean direction and resultant vector length computed with circstat toolbox (Matlab, Mathworks). (iii) Equation used for fitting the phase distribution and quantify locking: specific elements used for calculating phase-locking depth are color-coded and shown also on example distribution in (ii). Red, fitted function. Cyan, amplitude/gain. Brown, preferred phase. Green, baseline (mean firing rate/DC). Locking depth is calculated as 2×a/(2×a+c).

FIG. 10c illustrates neuronal units in contralateral hemisphere exhibit a larger shift in firing properties during stimulation blocks: Change in phase-locking-depth of spiking activities in individual neuronal clusters to MTL iEEG slow waves (FIG. 3) during 'stim' blocks relative to the NREM block before stimulation session ('PRE'), separately for clusters ipsilateral (blue) or contralateral (yellow) to stimulation site. Note that change in phase locking depth is driven by contralateral neuronal clusters (n=150, sign-test: *P<$10^{-3}$) rather than ipsilateral clusters (n=117, sign-test, P=0.06).

FIG. 10d illustrates separate distributions of change in phase-locking-depth for different brain areas. Orange, MTL (medial temporal lobe including hippocampus, entorhinal cortex and parahippocampal gyrus). Light green, Am (amygdala). Dark green, OF, AF, In (orbitofrontal cortex, anterior prefrontal cortex, and insula). Cyan, Par (parietal cortex). Blue, Occ (occipital cortex).

FIG. 10e illustrates phase locking depth of neuronal clusters to MTL iEEG slow wave persists beyond the 'stim' block: a comparison between the first 5 min 'pause' block to the NREM block before stimulation session ('PRE') reveals significantly enhanced phase-locking depth change (orange) compared to shuffled distribution (gray, P<$10^{-8}$ via Wilcoxon test).

FIG. 10f illustrates persistent effect of iEEG correlations: scatterplot of iEEG inter-regional correlation in pairs of electrodes (iEEG in MTL probe vs. any other location) following the first 'stim' block (y-axis) vs. 'pre-stim' block before any stimulation blocks (x-axis). Each dot corresponds to a difference in a pair of iEEG electrodes: from sync-stimulation in OF neocortex (red) or other areas orange): from mixed-phase stimulation in OF neocortex (gray): n=138 iEEG electrodes (most medial contact) in n=14 subjects.

FIG. 10g illustrates inter-regional cross-correlation in pairs of electrodes (iEEG in MTL probe vs. any other location) increases following first stimulation block for synch-stimulation group (red, stim delivered in OF cortex, *P<10$^{-5}$, n=51 iEEG contacts, orange, stim in other areas, *P<10$^{-2}$, n=26 iEEG contacts) but not for the mixed-phase stimulation group (gray, P=0.24, n=61 iEEG contacts, all P values via Wilcoxon sign-rank test).

Figure 11:
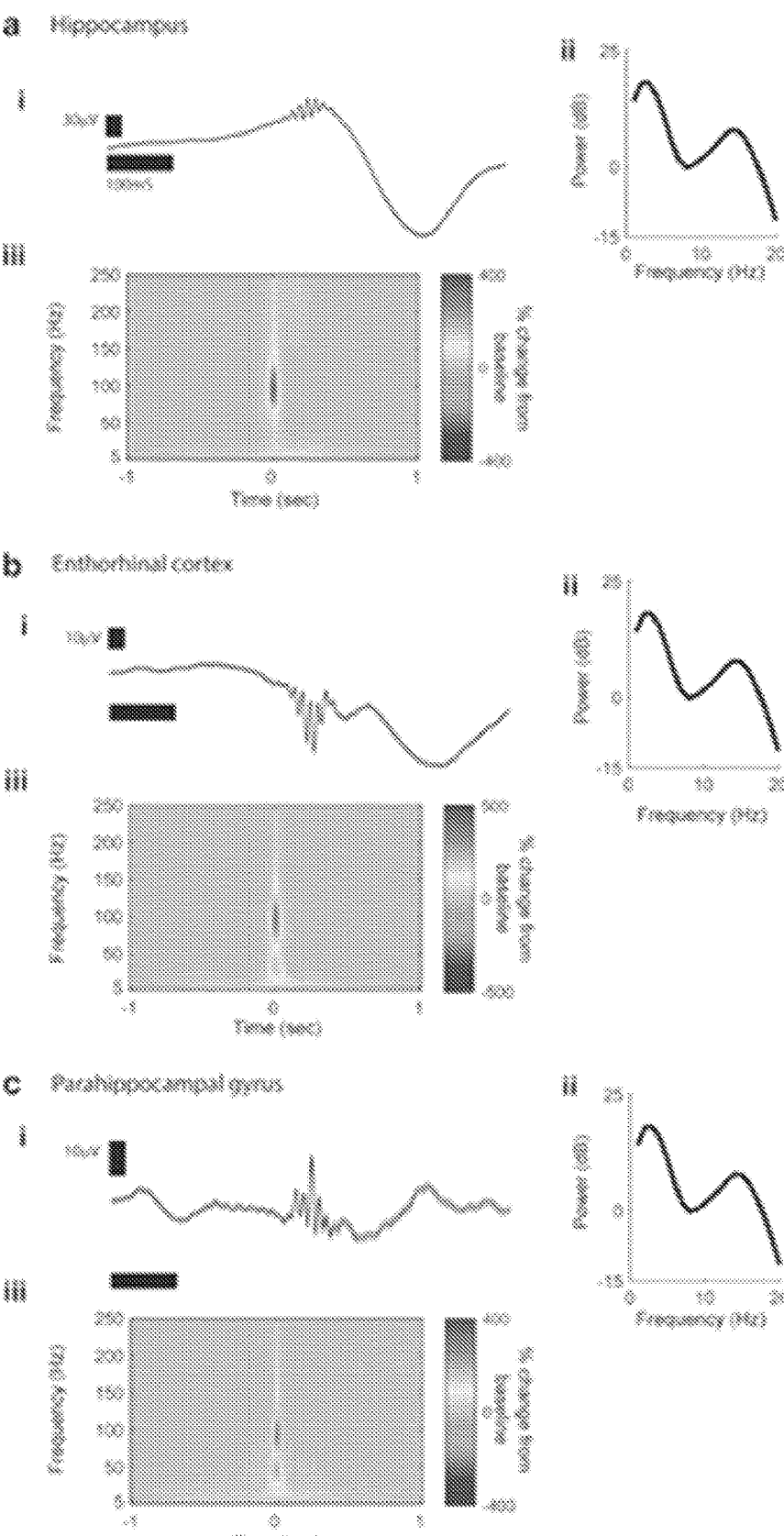

FIGS. 11a-11c illustrate ripple characteristics in specific MTL regions.

FIG. 11a illustrates detected ripples in iEEG electrodes targeting hippocampus. FIG. 11a(i) shows grand average of raw unfiltered iEEG traces (n=3687 events in 14 electrodes/10 participants, mean±SEM) aligned to the maximum of the ripple peak (time 0) during pre-stim epochs. FIG. 11a(ii) shows an average power spectrum (1-20 Hz, 0.5 Hz resolution) of iEEG traces (+1 sec around detected ripples) reveals peaks at ~3 Hz (slow waves) and ~14 Hz (fast sleep spindles). FIG. 11a(iii) illustrates average of ripple-peak-locked TFR (time-frequency representation, % change from pre-event baseline, color bar on right) highlights the band-limited nature of ripples around 80-120 Hz.

FIG. 11b shows the same format as FIG. 11a for detected ripples in iEEG traces of electrodes targeting entorhinal cortex (n=2986 events in 12 electrodes/8 participants).

FIG. 11c shows the same format as FIG. 11a for detected ripples in iEEG traces of electrodes targeting parahippocampal cortex (n=596 events in 5 electrodes/5 participants). Calibration bars mark 100 ms and 30 μV (hippocampus) or 10 μV (other MTL regions).

FIGS. 12a-12e illustrate coupling of sleep oscillation between MTL and neocortex.

Figure 1:
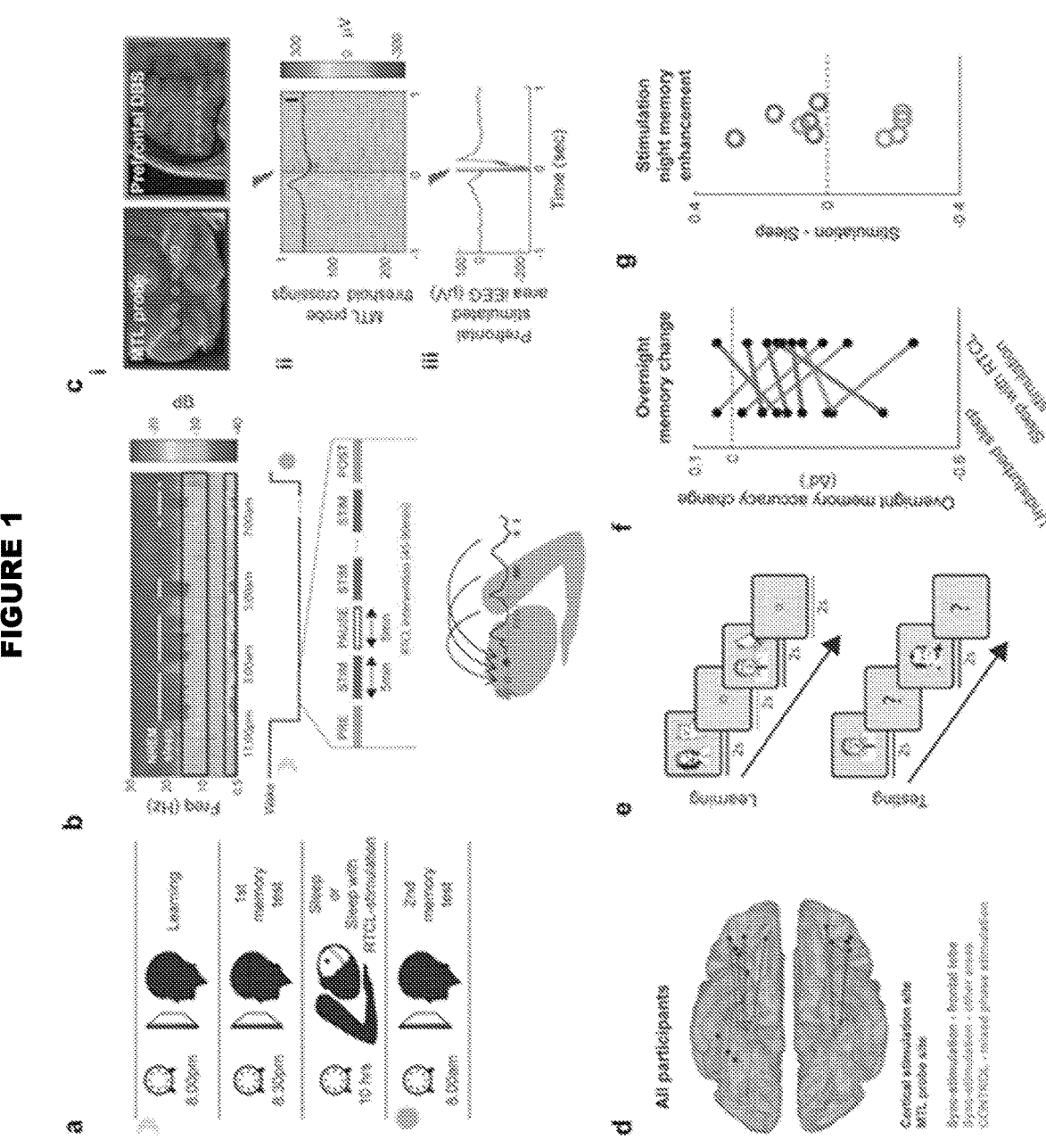
FIGS. 1a-1g illustrate neocortical stimulation synchronized to MTL sleep activity improves overnight recognition memory specificity.
Figure 5:
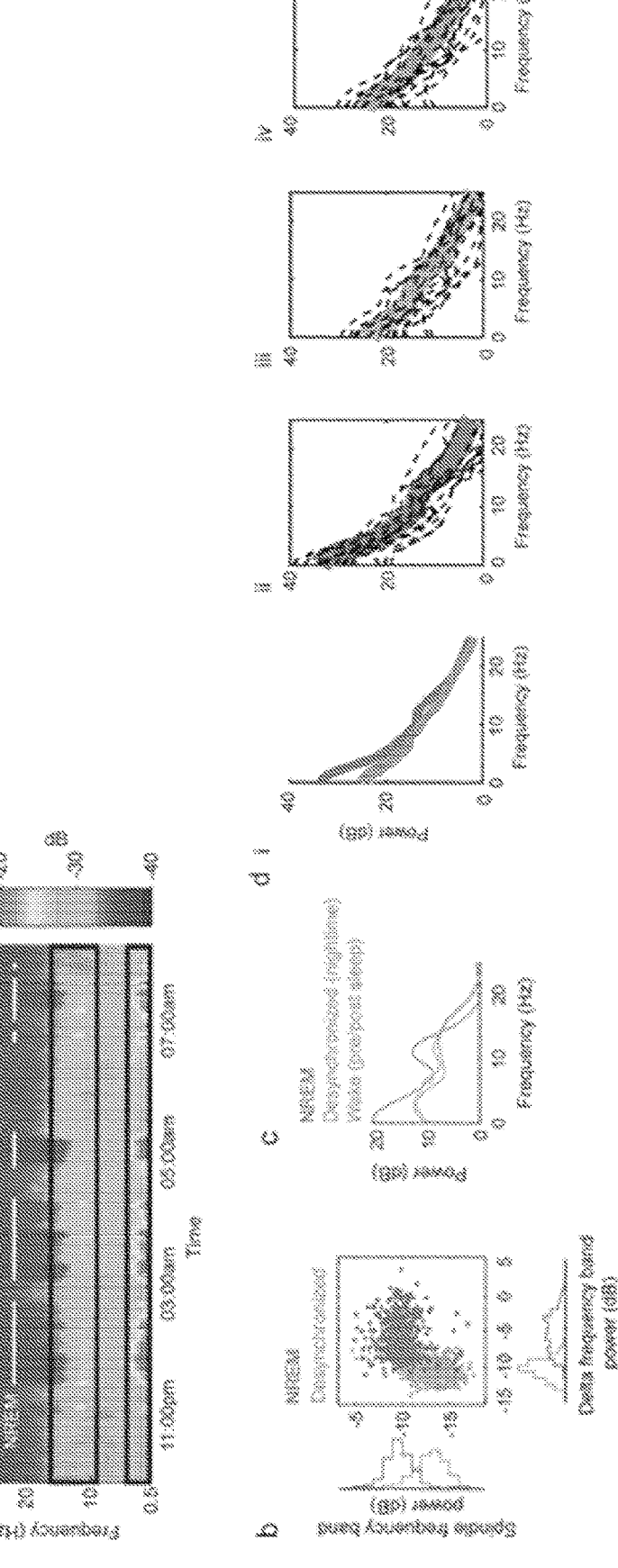
Figure 12:
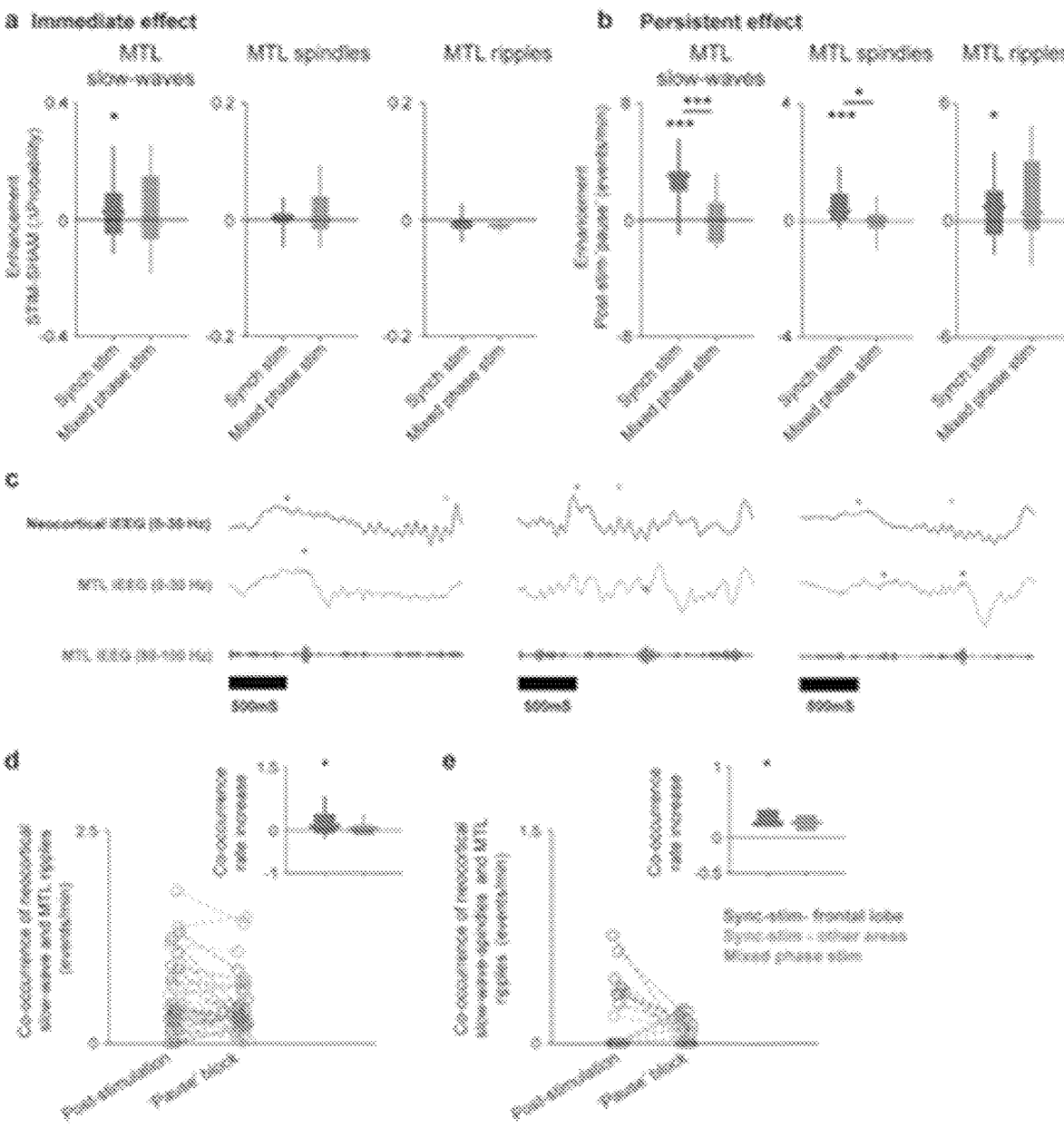

FIG. 12a illustrates an immediate effect of stimulation in MTL. iEEG electrodes in sync-stim patients exhibit an increase in slow-wave detection probability in 3 sec following stimulations, relative to sham stimulation points (matched to real stimulation phase) during 'pause' blocks (Methods Section), while spindle (middle), and ripple (right) probability is not significantly different immediately following stimulations. Red (left bars), MTL contacts in sync-stimulation patients. Gray (right bars), MTL contacts in mixed-phase stimulation. Wilcoxon sign rank test for each bar: P=0.04, P=0.1, P=0.9 for slow wave/spindle/ripple in sync-stim group (red bars), P=0.5, P=0.2, P=1 for slow wave/spindle/ripple in mixed-stim group (gray bars). No significant difference was found between stimulation-mode groups (Wilcoxon rank-sum test P>0.05). Note that ripple probability is calculated over 200 msec following stimulation/sham events and that stimulation was delivered in neocortical sites, distant from MTL (FIGS. 1D and 5).

FIG. 12b illustrates a lingering effect of stimulation in MTL. A comparison of event rate during 1-min following stimulation blocks to the rest of the 'pause' block demonstrates an increase in MTL slow waves, spindles and ripple rate for sync-stim patients (red) but not for mixed-phase patients (gray). Red (left bars), MTL contacts in sync-stimulation. Gray (right bars), MTL contacts in mixed-phase stimulation. *P<104, *P<10$^{-3}$, *P=0.03 for slow wave/spindle/ripple in sync-stim group (red bars), P=0.5, P=0.4, P=0.1 for slow wave/spindle/ripple in mixed-stim group (gray bars)—all p-values assessed via Wilcoxon sign-rank test. Wilcoxon rank sum test comparing stimulation-mode group (sync-stim vs mixed-stim): ***P<10$^{-3}$, *P=0.02, P=0.7 for slow wave/spindle/ripple rate increase. Note that stimulation was delivered in neocortical sites, distant from MTL (FIGS. 1d and 6).

FIG. 12c are examples of triple co-occurrence of cortical slow-wave-spindles with MTL-ripple events (participants 2 and 14): each example displays simultaneous recordings from a pair of iEEG electrodes in neocortex (black, top row, 0-30 Hz), MTL (blue, middle row, 0-30 Hz) and a ripple band (80-100 Hz) band-pass filtered trace of the MTL iEEG (bottom row). Brown star, detected ripple: Purple, detected slow-wave positive iEEG peak ('OFF' period), pink—detected spindle event.

FIG. 12d illustrates a double co-occurrence rate of neocortical slow-waves and MTL ripples increases in the 1-min interval post-stimulation blocks (left) and decreases during the remaining 'pause' block (right, ~4 min). Inset is post-stim rate vs 'pause' rate, pulling together red and orange couples to the red group (red, n=22 electrode pairs, *P=0.018 in sync-stimulation group: gray, n=11, P=0.3 in mixed-phase group via Wilcoxon signed-rank tests).

FIG. 12e illustrates a triple occurrence of slow-waves and spindle in neocortical iEEG channels with ripple on MTL iEEG (Methods). (red, n=5 electrode pairs, *P=0.03 in sync-stimulation group: gray, n=2, P=0.2 in mixed-phase group via Wilcoxon signed-rank tests).

FIGS. 13a and 13b illustrate pathological interictal epileptiform discharges (IEDs).

FIG. 13a(i) illustrates a grand average of 6175 unfiltered iEEG traces during pre-stim intervals (mean±SEM) in 66 electrodes with prevalent IED activity based on visual review and neurologist definition (n=8 subjects), aligned to the maximum IED peak (time 0) (see Methods for IED detection parameters). Note that these channels were excluded from main analyses based on high rate of abnormal activity. FIG. 13a(ii) illustrates an average of IED-locked TFR (% change from pre-event baseline, colorbar on right), highlighting the wide-band and high-frequency spectral profile of IEDs. FIG. 13a(iii) illustrates a grand average iEEG power spectrum (0.1 Hz resolution) around (±1 s) detected IED events.

FIG. 13b illustrates effects of stimulation on overnight memory accuracy enhancement (y-axis) vs. change in IED rates (x-axis) do not reveal a consistent relationship. X-axis: distribution of IED rate change during 'pause' blocks relative to pre-sleep baseline (%): distribution is calculated for 10 participants who underwent cognitive testing, total of N=417 iEEG channels including high-rate channels that were removed from sleep-activity analysis. Y-axis: Overnight change in recognition memory accuracy intervention night relative to undisturbed sleep (Δd', see Methods). Distribution color depicts stimulation type: Red, sync-stimulation in prefrontal cortex. Orange, sync-stimulation in other neocortical regions. Gray, mixed-phase stimulation in prefrontal cortex. Black crosses mark the median of each subject's values across all iEEG electrodes (shown as distribution). Note that IED rate change per participant (median score for all iEEG electrodes in every patient) had no significant correlation with memory accuracy enhancement (Spearman correlation: ρ=−0.21, P=0.5, n=10 subjects).

FIG. 14 illustrates patient demographics and clinical information. The columns in FIG. 14 are: (i) Participant id (n=14), (ii) Age, (iii) Gender (M/F=Male/Female), (iv) Handedness (R/L=Right/Left), (v) Seizure onset area: (vi) Resection/Outcome: RNS: Responsive NeuroStimulator.

(vii) Imaging FDG-PET, and (viii) MRI. Abbrev.: LaFSG—Left anterior fusiform gyrus, LaMTL—left anterior medial temporal lobe, R/LIN—right/Left insula, LiT—left inferior temporal, R/LTL—right/left temporal lobe, MTL—medial temporal lobe, Rp—right posterior, RPHG—right parahippocampal gyrus, RPNH—right posterior nodular heterotopia, SMA—supplementary motor area.

Figure 15:
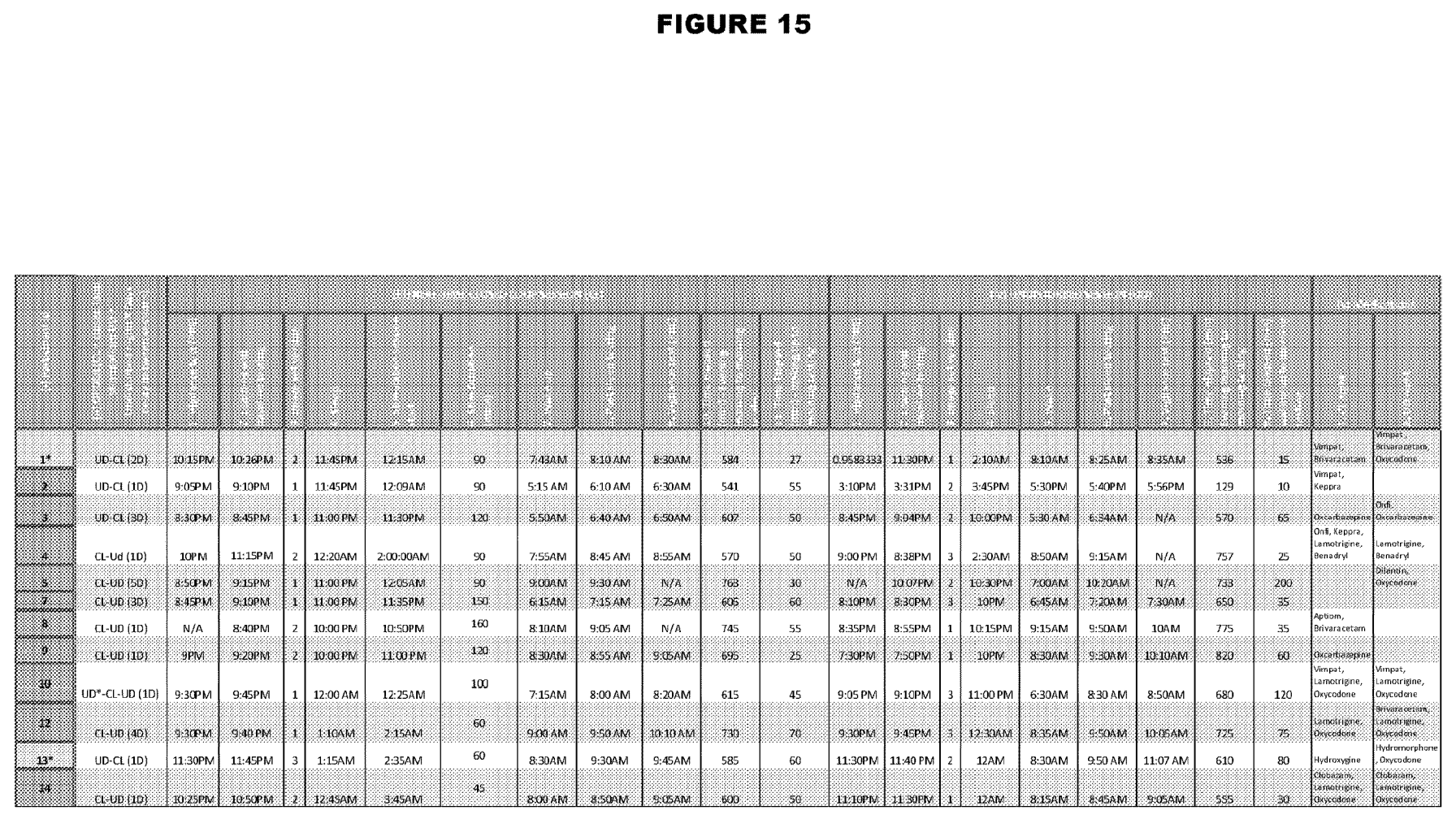

FIG. 15 illustrates cognitive testing details. The columns in FIG. 15 are: (i) Participant id of subset of participants with cognitive testing, asterisks denote 2 participants who were excluded (Methods, p1 and p13) from memory accuracy statistics but included in neurophysiology analysis. (ii) Order of testing nights–CL=RTCL intervention night, UD=undisturbed night. Parentheses is number of days between experimental nights. (iii) Sub-columns for each intervention experimental night—time of day (TOD) for (1) vigilance testing: (2) learning and testing in memory paradigm: (3) test version (3 different sets of images): (4) Sleep start TOD as recorded by an observer based on patient's EEG signals: (5) Stimulation session start TOD: (6) Stimulation session duration (comprised as intermittent stimulation and pause blocks as described in FIG. 1B): (7) Wake up TOD: (8) morning testing TOD: Time elapsed (min) between (9) evening learning to morning testing and (10) wake-up to testing. (iv) Sub-columns for each un-disturbed experimental night—same as (iii) w/o the stimulation-related columns. (v) Participant's drug regimen during (1) CL intervention nights and (2) undisturbed nights.

FIG. 16 illustrates real-time closed loop intervention night information. Shaded rows are intervention sessions with full cognitive testing that are also reported in FIGS. 1f, 1g, and 15. The shading corresponds to stimulation type listed in rightmost column, white background sessions are included in neurophysiology analysis. the columns (left to right) are: (1) Intervention session number: (2) Participant number (participant #12 participated in two intervention nights): (3) Start of session time of day: (4) Number of stimulation blocks per session (5) Total length of session (first stim-block till end of last stim-block) (min): (6) Stimulation type—unipolar/bipolar: (7) Stimulation hemisphere and approximate location (exact scans in FIG. 5): (8) Location of MTL-probe used as input to RTCL system: (9) Number of iEEG electrodes recorded in session (note that there are 6-8 iEEG contacts per electrode): (10) RTCL mode—sync-stim (red—stimulation site in prefrontal cortex, orange—in other anatomical areas)/mixed-phase stim (gray). Abbreviations: *R=right, L=Left: **AH=Anterior Hippocampus (hip), MH=Medial hip, EC=Entorhinal cortex, PHG=Parahippocampal gyrus.

Figure 17:
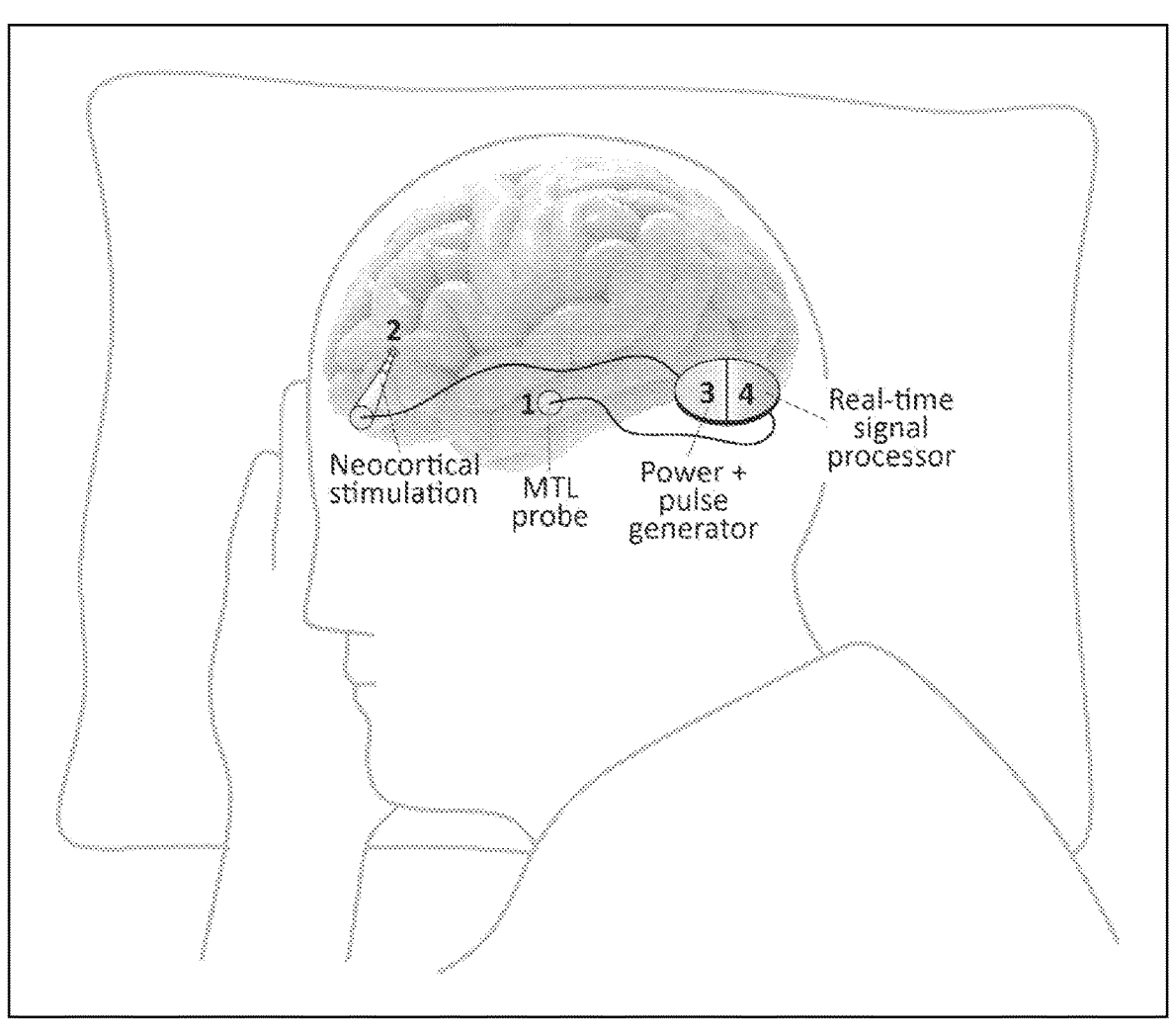

FIG. 17 illustrates a system for real-time closed loop stimulation of the brain. The system includes a first implanted electrode (e.g., an intracranial EEG (iEEG) electrode, a medial temporal lobe (MTL) probe as illustrated in FIG. 17) that serves as a synchronization-probe for closed-loop control. The system also includes a second implanted electrode (e.g., a neocortical iEEG electrode, neocortical stimulation probe as illustrated in FIG. 17) that served as the stimulation site. The second implanted electrode is electrically coupled to the first implanted electrode via closed loop control. The system also includes one or more processors. The stimulation pulses (see Methods Section) can be generated and applied in real-time, using the power and pulse generator, in accordance with some embodiments of the present disclosure.

Figure 18:
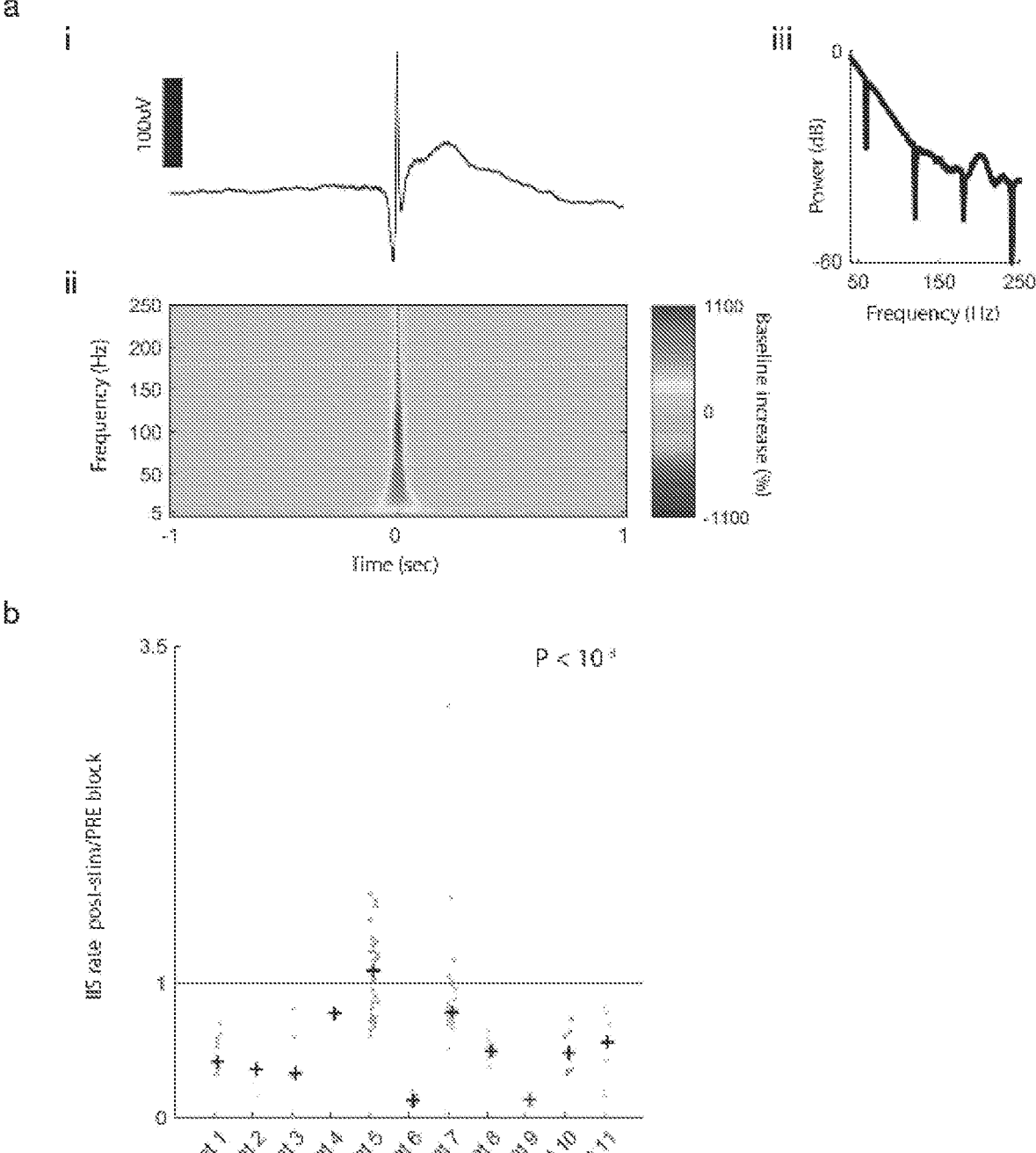

FIGS. 18a and 18b illustrate reduction of pathological epileptic activity by prefrontal deep brain stimulation synchronized to MTL during sleep.

FIG. 18a(i) illustrates a grand average of 6175 unfiltered iEEG traces during pre-stimulation intervals (mean±SEM) in 66 electrodes with prevalent interictal epileptic discharge (IED activity), aligned to the maximum IED peak (time 0). FIG. 18a(ii) illustrates an average of IED-locked time-frequency dynamics (% change from pre-event baseline), highlighting the wide-band and high-frequency spectral profile of IEDs. FIG. 18a(iii) illustrates a grand average power spectrum (0.1 Hz resolution) of iEEG data around (±1 s) detected IED events reveals elevated power around 200 Hz, attesting to successful detection of pathological events.

FIG. 18b illustrates effects of stimulation on IED occurrence (difference between IED rate after stimulation to the IED rate in the same iEEG channel before stimulation, y-axis) in each participant separately (x-axis). Colored dots mark individual iEEG channels in each participant (a total of N=118 channels with significant pathological activity at baseline in 11 individuals). Black crosses mark the median ratio (post stimulation divided by pre-stimulation) across channels in each participant. The results reveal robust and consistent reduction of pathological epileptic activity (rate is lower, i.e., below ratio of 1, in 10/11 individuals: $p<10^{-3}$ via Wilcoxson sign-rank test when applying a conservative statistical test considering each individual (rather than each electrode) as an independent sample)

Figure 19:
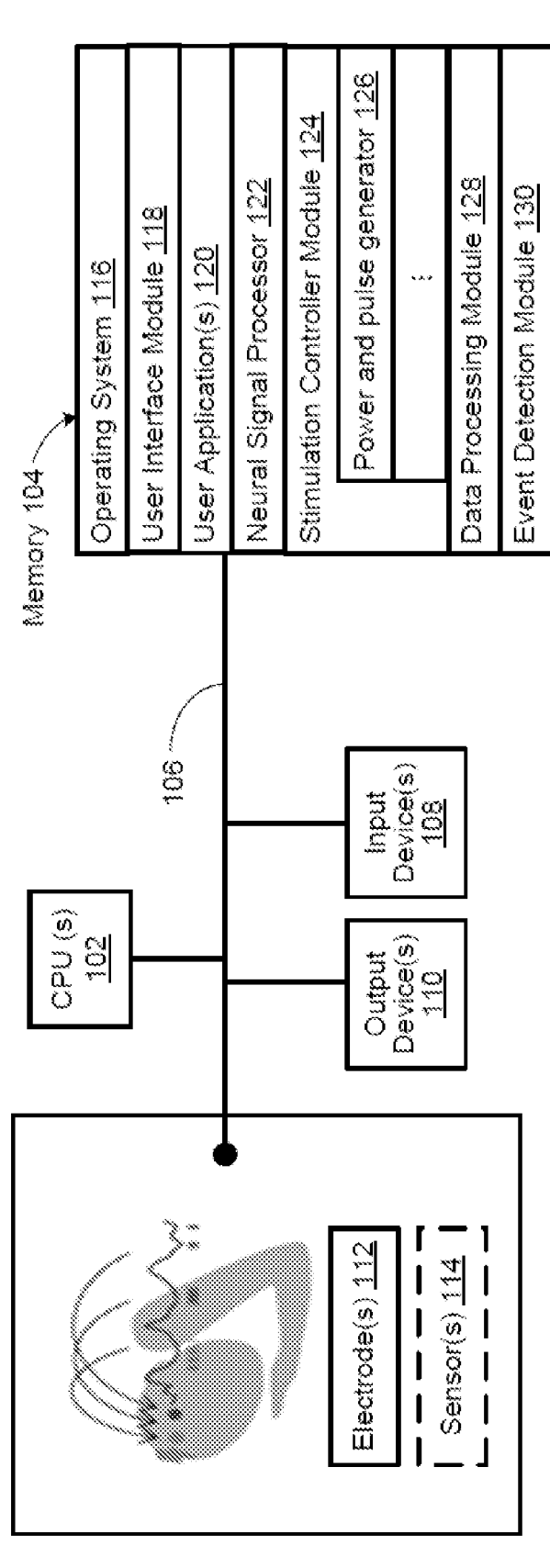

FIG. 19 illustrates a block diagram illustrating a system configured to perform real-time closed loop (RTCL) stimulation of a brain of a human subject, in accordance with some embodiments.

DETAILED DESCRIPTION

Reference will now be made to implementations, examples of which are illustrated in the accompanying drawings. In the following description, numerous specific details are set forth in order to provide a thorough understanding of the present invention. However, it will be apparent to one of ordinary skill in the art that the present invention may be practiced without requiring these specific details.

For decades, sleep has been demonstrated to play a critical role in long term memory consolidation. Systems-level memory consolidation theory posits that initial memory encoding is primarily supported by the hippocampus, but over time, memory representations become increasingly dependent upon the neocortex (a 'two-stage' model). A central notion in this model is that embedding novel information in the neocortex relies on offline reactivation of acquired information by the hippocampus around ripple events, co-occurring with neocortical slow waves and thalamo-cortical sleep spindles that prime neocortical circuits for synaptic plasticity.

Slow waves (<4 Hz) reflect regionally-synchronous alternations between active states of membrane depolarization and spiking, and inactive states of hyperpolarization and neuronal quiescence. Slow waves are thought to play a role in overnight memory consolidation through the synchronization of sleep spindle (9-16 Hz) and hippocampal ripple oscillations (~80-120 Hz in humans) around active slow waves states, and possibly also by mediating synaptic downscaling. Given the difficulty of detecting hippocampal ripples non-invasively, most evidence supporting the active consolidation theory stems from invasive recordings in rodents and is mostly correlative.

The present disclosure describes a closed-loop stimulation protocol that is designed to dynamically and selectively enhance the temporal coupling between hippocampal ripples and neocortical slow waves and spindles during non-rapid eye movement (NREM) sleep, so as to establish a causal link between increased hippocampo-cortical coupling and human memory consolidation.

Neurosurgical patients with pharmacoresistant epilepsy, implanted with intracranial depth electrodes (n=14, ages 23-47 years, 9 women, all fluent English speakers, FIG. 14) provided written informed consent before participation in a UCLA IRB-approved study. To assess cognitive effects, participants were tested during two experimental nights (order counterbalanced): an intervention night and an undisturbed night (see FIG. 1a and FIG. 15). This within-subject design helped control for individual variability in memory profiles. On the intervention night, real-time closed-loop (RTCL) stimulation was performed intermittently in 5-minute blocks for a total of ~90 min during early NREM sleep (see Methods Section, FIGS. 1b, 5, and 16). One intracranial EEG (iEEG) electrode in the MTL served as a synchronization-probe for closed-loop control, while a second neocortical iEEG electrode served as the stimulation site (typically, in 12 out of 15 stimulation nights, in orbitofrontal cortex white matter. See FIGS. 1c, 1d, 5, and 6). Slow wave activity in the MTL probe was monitored and analyzed in real-time to trigger brief (e.g., 50 msec) high-frequency (e.g., 100 Hz) electrical stimulation events in the neocortical stimulation site (See Methods section). The closed-loop intervention had two modes of operation—either (i) 'synchronized (sync) stimulation' (FIGS. 1c and 1d, red) or (ii) 'mixed-phase stimulation' (gray in FIG. 1d). In sync stimulation aimed at synchronizing MTL and neocortical activities, neocortical stimulations were time-locked to the MTL slow-wave active phase (iEEG negative peak). In mixedphase stimulation serving as a control, neocortical stimulations were applied without regard to the MTL slow-wave phase (See Methods Section and FIG. 7).

To assess effects of the intervention on overnight memory consolidation, participants performed a visual paired-association task before sleep, learning pairings between photos of famous people and animals on the evening before each experimental night (FIG. 1e, Methods Section, different set of images before first and second nights). Two aspects of memory performance were assessed: (i) accuracy—discrimination of learned people vs. a set of lures, and (ii) association: pairing each person to its associated animal. Performance was tested twice: several minutes following learning, as well as after overnight sleep (FIG. 1a). Performance change between evening and morning tests was compared for intervention and undisturbed sleep nights, for each subject separately (10 participants with full cognitive testing suite, Methods, FIG. 15). In 5 out of 5 participants receiving sync-stimulation in prefrontal cortex white matter, memory accuracy (Δd', Methods, *P<0.05 based on a binomial model) following the intervention night was superior to that following undisturbed sleep (FIGS. 1f and 1g, red). Mixed results were observed for sync-stimulation delivered in other neocortical regions (FIGS. 1f and 1g, n=2, orange), and no improvement was evident for subjects who received mixed-phase stimulation (FIGS. 1f and 1g, n=3, gray). Stimulation did not reliably affect the pairing (association) accuracy (FIGS. 8a and 8b). Reaction times during memory recall were not significantly different following sleep with sync-stimulation compared with undistributed sleep (Wilcoxon rank-sum test: P=0.68, FIG. 8c(i)). Conversely, reaction times in a visual psychomotor vigilance task (PVT, Methods Section) deteriorated following sleep with stimulation as compared with undisturbed sleep (FIG. 8c(ii)), suggesting that memory improvement does not reflect an across-the-board change in vigilance.

What is claimed is:

1. A closed-loop neuromodulatory system, comprising:
one or more processors; and
memory storing instructions for execution by the one or more processors, the stored instructions including instructions for:
recording signals from a first region of a brain of a human subject during sleep via a first electrode;
determining, from the recorded signals, slow-wave activity periods of the first region; and
applying, in real-time via a second electrode that is electrically coupled to the first electrode via closed-loop control, one or more electrical stimulations to a second region of the brain, wherein the second region of the brain is different from the first region of the brain, and the applying includes time-locking the one or more electrical stimulations with the slow-wave activity periods of the first region.

2. The system of claim 1, wherein the instructions for applying, in real time, the one or more electrical stimulations to the second region of the brain include instructions for:
applying, in real-time, electric pulses having a frequency of around 100 Hz.

3. The system of claim 2, wherein the stored instructions further include instructions for:
applying the electric pulses intermittently via a plurality of time blocks.

4. The system of claim 3, wherein the plurality of time blocks includes alternating stimulation and pause intervals.

5. The system of claim 4, wherein the alternating stimulation and pause intervals include a plurality of stimulation events, each having a respective pulse shape, pulse width, and frequency.

6. The system of claim 5, wherein each of the stimulation events includes a current ranging from 0.5 to 1.5 mA.

7. The system of claim 3, wherein the plurality of time blocks includes a plurality of time blocks during specific stages of sleep.

8. The system of claim 1, wherein:
the first region of the brain includes the medial temporal lobe (MTL); and
the second region of the brain includes prefrontal white matter.

9. The system of claim 1, wherein the first and second electrodes are implanted in the brain.

10. The system of claim 1, wherein the stored instructions further include instructions for:
stimulating the second region of the brain for a time duration of 45-140 minutes.

11. A method, comprising:
recording signals from a first region of a brain of a human subject during sleep via a first electrode;
determining, from the recorded signals, slow-wave activity periods of the first region; and
applying, in real-time via a second electrode that is electrically coupled to the first electrode via closed-loop control, one or more electrical stimulations to a second region of the brain, wherein the second region of the brain is different from the first region of the brain, and the applying includes time-locking the one or more electrical stimulations with the slow-wave activity periods of the first region.

12. The method of claim 11, wherein applying, in real time, the one or more electrical stimulations includes applying, in real-time, electric pulses having a frequency of around 100 Hz.

13. The method of claim 11, further comprising:

determining from the recorded signals one or more events, including one or more of: neocortical slow-waves, thalamo-cortical sleep-spindles, hippocampal-ripples, neuronal replay sequences, REM-sleep theta bursts, and other sleep activities, wherein the second region of the brain is stimulated in accordance with the determined one or more events.

14. The method of claim 11, wherein applying, in real time, the one or more electrical stimulations to the second region of the brain comprises applying, in real-time, electric pulses that are synchronous with one or more particular phases of slow wave recorded in the first region.

15. The method of claim 11, wherein applying, in real time, the one or more electrical stimulations to the second region of the brain comprises applying, in real-time, electric pulses that are synchronous with ripples in the first region.

16. The method of claim 11, wherein the signals are recorded during a NREM sleep state of the human subject.

17. The method of claim 11, wherein:

the first region of the brain comprises the medial temporal lobe (MTL); and the second region of the brain comprises prefrontal white matter.

18. The method of claim 11, further comprising, prior to applying the one or more electrical stimulations to the second region of the brain:

determining, via polysomnography, that the human subject has experienced at least 30 minutes of consolidated sleep.

19. The method of claim 11, wherein the steps of recording, determining, and applying are implemented as part of a treatment of epilepsy or other neurological conditions characterized by epileptic-like activity.

20. A non-transitory computer-readable storage medium having instructions stored thereon, which when executed by one or more processors, cause the processors to perform operations comprising:

recording signals from a first region of a brain of a human subject during sleep via a first electrode;

determining, from the recorded signals, slow-wave activity periods of the first region; and applying, in real-time via a second electrode that is electrically coupled to the first electrode via closed-loop control, one or more electrical stimulations to a second region of the brain, wherein the second region of the brain is different from the first region of the brain, and the applying includes time-locking the one or more electrical stimulations with the slow-wave activity periods of the first region.

\* \* \* \* \*